US008597227B2

(12) United States Patent
Childers et al.

(10) Patent No.: US 8,597,227 B2
(45) Date of Patent: Dec. 3, 2013

(54) WEIGHT/SENSOR-CONTROLLED SORBENT SYSTEM FOR HEMODIALYSIS

(75) Inventors: Robert W. Childers, Trinity, FL (US); David S. Brown, Gurnee, IL (US); Ramesh Wariar, Tampa, FL (US); Sujatha Karoor, Lake Bluff, IL (US); Shahid Din, Palm Harbor, FL (US); Leo Martis, Long Grove, IL (US); Cody Buchmann, Columbus, OH (US); Paul Soltys, Holmdel, NJ (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/213,707

(22) Filed: Aug. 19, 2011

(65) Prior Publication Data

US 2011/0303590 A1 Dec. 15, 2011

Related U.S. Application Data

(63) Continuation of application No. 12/562,730, filed on Sep. 18, 2009, now Pat. No. 8,357,113, which is a continuation of application No. 10/623,316, filed on Jul. 17, 2003, now Pat. No. 7,867,214.

(60) Provisional application No. 60/397,131, filed on Jul. 19, 2002.

(51) Int. Cl.
*A61M 1/00* (2006.01)

(52) U.S. Cl.
USPC .......................................... 604/27

(58) Field of Classification Search
USPC ........................................... 604/29
See application file for complete search history.

(56) References Cited

U.S. PATENT DOCUMENTS

| | | |
|---|---|---|
| 2,529,028 A | 7/1947 | Landon |
| 2,122,509 A | 7/1948 | Beliaeff |
| 3,332,737 A | 7/1967 | Krause |
| 3,388,803 A | 6/1968 | Scott |
| 3,463,728 A | 8/1969 | Kolobow et al. |
| 3,485,245 A | 12/1969 | Lahr et al. |

(Continued)

FOREIGN PATENT DOCUMENTS

| | | |
|---|---|---|
| DE | 19828923 | 1/2000 |
| DE | 19814695 | 9/2001 |

(Continued)

OTHER PUBLICATIONS

"Fresnius 90/2 Peritoneal Therapy Cylcer" Article, written by Fresenius USA, dated Jul. 1993.

(Continued)

*Primary Examiner* — Victoria P Shumate
(74) *Attorney, Agent, or Firm* — K&L Gates LLP

(57) ABSTRACT

A hemodialysis system including (i) a dialyzer; (ii) a blood circuit including a blood pump in fluid communication with the dialyzer; (iii) a dialysate circuit including a dialysate circulation pump in fluid communication with the dialyzer, the dialysate circuit further including a sorbent cartridge for cleaning used dialysate; (iv) a container holding an initial supply of dialysate; (v) a container pump in fluid communication with the dialysate circuit and the container; (vi) a supply of concentrate; and (vii) an electronic weight balance positioned and arranged to weigh the supply of concentrate.

22 Claims, 10 Drawing Sheets

(56) References Cited

U.S. PATENT DOCUMENTS

| | | |
|---|---|---|
| 3,490,479 A | 1/1970 | Mott et al. |
| 3,528,550 A | 9/1970 | Cappelen, Jr. |
| 3,545,438 A | 12/1970 | De Vries |
| 3,608,729 A | 9/1971 | Haselden |
| 3,617,545 A | 11/1971 | Dabois et al. |
| 3,619,423 A | 11/1971 | Galletti et al. |
| 3,667,612 A | 6/1972 | Leonard |
| 3,669,878 A | 6/1972 | Marantz et al. |
| 3,669,880 A | 6/1972 | Marantz et al. |
| 3,682,817 A | 8/1972 | Marx |
| 3,697,418 A | 10/1972 | Johnson |
| 3,703,959 A | 11/1972 | Raymond |
| 3,707,967 A | 1/1973 | Kitrilakis et al. |
| 3,727,612 A | 4/1973 | Sayers et al. |
| 3,730,183 A | 5/1973 | Goldsmith et al. |
| 3,799,873 A | 3/1974 | Brown |
| 3,809,241 A | 5/1974 | Alvine |
| 3,825,493 A | 7/1974 | Brown et al. |
| 3,827,975 A | 8/1974 | Bizot et al. |
| 3,850,835 A | 11/1974 | Marantz et al. |
| 3,878,564 A | 4/1975 | Yao et al. |
| 3,884,808 A | 5/1975 | Scott |
| 3,911,915 A | 10/1975 | Seifter et al. |
| 3,926,797 A | 12/1975 | Gigou et al. |
| 3,939,069 A | 2/1976 | Granger et al. |
| 3,979,284 A | 9/1976 | Granger et al. |
| 3,989,622 A | 11/1976 | Marantz et al. |
| 4,000,072 A | 12/1976 | Sato et al. |
| 4,031,010 A | 6/1977 | Nose |
| 4,036,747 A | 7/1977 | Hori et al. |
| 4,081,372 A | 3/1978 | Atkin et al. |
| 4,115,259 A | 9/1978 | Bigi |
| 4,118,314 A | 10/1978 | Yoshida |
| 4,173,537 A | 11/1979 | Newhart et al. |
| 4,180,460 A | 12/1979 | Calari |
| 4,190,047 A | 2/1980 | Jacobsen et al. |
| 4,191,646 A | 3/1980 | Larsson et al. |
| 4,192,748 A | 3/1980 | Hyden |
| 4,194,536 A | 3/1980 | Stine et al. |
| 4,212,738 A | 7/1980 | Henne |
| 4,213,859 A | 7/1980 | Smakman et al. |
| 4,229,299 A | 10/1980 | Savitz et al. |
| 4,240,408 A | 12/1980 | Schael |
| 4,247,393 A | 1/1981 | Wallace |
| 4,256,718 A | 3/1981 | McArthur et al. |
| 4,267,040 A | 5/1981 | Schal |
| 4,267,047 A | 5/1981 | Henne et al. |
| 4,269,708 A | 5/1981 | Bounomini et al. |
| 4,276,175 A | 6/1981 | Bower |
| 4,293,762 A | 10/1981 | Ogawa |
| 4,303,521 A | 12/1981 | Lehmann |
| 4,313,831 A | 2/1982 | Lehmann et al. |
| 4,338,190 A | 7/1982 | Kraus et al. |
| 4,360,507 A | 11/1982 | McArthur et al. |
| 4,364,747 A | 12/1982 | Blackshear et al. |
| 4,381,003 A | 4/1983 | Buoncristiani |
| 4,460,555 A | 7/1984 | Thompson |
| 4,464,563 A | 8/1984 | Jewett |
| 4,473,449 A | 9/1984 | Michaels et al. |
| 4,498,900 A | 2/1985 | Buoncristiani |
| 4,532,414 A | 7/1985 | Shah et al. |
| 4,542,015 A | 9/1985 | Smakman et al. |
| 4,581,141 A | 4/1986 | Ash |
| 4,586,920 A | 5/1986 | Peabody |
| 4,618,343 A | 10/1986 | Polashegg |
| RE32,303 E | 12/1986 | Lasker et al. |
| 4,650,464 A * | 3/1987 | Ruiz et al. .................. 604/500 |
| 4,650,857 A | 3/1987 | May |
| 4,661,246 A | 4/1987 | Ash |
| 4,670,007 A * | 6/1987 | Wheeldon et al. ............ 604/65 |
| 4,678,460 A | 7/1987 | Rosner |
| 4,680,445 A | 7/1987 | Ogawa |
| 4,684,460 A | 8/1987 | Issautier |
| 4,702,829 A | 10/1987 | Polaschegg et al. |
| 4,703,913 A | 11/1987 | Hunkapiller |
| 4,718,890 A | 1/1988 | Peabody |
| 4,735,609 A | 4/1988 | Comeau et al. |
| 4,747,822 A | 5/1988 | Peabody |
| 4,765,907 A | 8/1988 | Scott |
| 4,769,151 A | 9/1988 | Shouldice |
| 4,804,474 A | 2/1989 | Blum |
| 4,844,074 A | 7/1989 | Kurucz |
| 4,847,470 A | 7/1989 | Bakke |
| 4,906,816 A | 3/1990 | van Leerdam |
| 4,950,259 A | 8/1990 | Geary et al. |
| 4,976,683 A | 12/1990 | Gauthier et al. |
| 5,004,459 A | 4/1991 | Peabody et al. |
| 5,073,167 A | 12/1991 | Carr et al. |
| 5,125,069 A | 6/1992 | O'Boyle |
| 5,141,492 A | 8/1992 | Dadson et al. |
| 5,141,493 A | 8/1992 | Jacobsen et al. |
| 5,180,896 A | 1/1993 | Gibby et al. |
| 5,227,820 A | 7/1993 | Miyashita et al. |
| 5,245,693 A | 9/1993 | Ford et al. |
| 5,284,470 A | 2/1994 | Beltz |
| 5,336,173 A | 8/1994 | Folden |
| 5,338,293 A | 8/1994 | Jeppsson et al. |
| 5,350,357 A | 9/1994 | Kamen et al. |
| 5,366,630 A | 11/1994 | Chevallet |
| 5,370,674 A | 12/1994 | Farrell |
| 5,381,510 A | 1/1995 | Ford et al. |
| 5,408,576 A | 4/1995 | Bishop |
| 5,420,962 A | 5/1995 | Bakke |
| 5,438,510 A | 8/1995 | Bryant et al. |
| 5,470,483 A | 11/1995 | Bene et al. |
| 5,474,683 A | 12/1995 | Bryant et al. |
| 5,498,338 A | 3/1996 | Kruger et al. |
| 5,522,998 A | 6/1996 | Polaschegg |
| 5,542,919 A | 8/1996 | Simon et al. |
| 5,641,405 A | 6/1997 | Keshaviah et al. |
| 5,643,201 A | 7/1997 | Peabody et al. |
| 5,645,734 A | 7/1997 | Kenley et al. |
| 5,683,381 A | 11/1997 | Carr et al. |
| 5,685,988 A | 11/1997 | Malchesky |
| 5,685,989 A | 11/1997 | Krivitski et al. |
| 5,690,614 A | 11/1997 | Carr et al. |
| 5,722,947 A | 3/1998 | Jeppsson et al. |
| 5,724,478 A | 3/1998 | Thweatt |
| 5,729,653 A | 3/1998 | Magliochetti et al. |
| 5,762,782 A | 6/1998 | Kenley et al. |
| 5,774,042 A | 6/1998 | Johnston |
| 5,790,752 A | 8/1998 | Anglin et al. |
| 5,816,779 A | 10/1998 | Lawless et al. |
| 5,836,908 A | 11/1998 | Beden et al. |
| 5,858,238 A | 1/1999 | McRea et al. |
| 5,873,853 A | 2/1999 | Keilman et al. |
| 5,875,282 A | 2/1999 | Jordan et al. |
| 5,876,611 A | 3/1999 | Shettigar |
| 5,902,336 A | 5/1999 | Mishkin |
| 5,919,369 A | 7/1999 | Ash |
| 5,921,951 A | 7/1999 | Morris |
| 5,938,634 A | 8/1999 | Packard |
| 5,944,684 A | 8/1999 | Roberts et al. |
| 5,960,160 A | 9/1999 | Clark et al. |
| 5,980,481 A | 11/1999 | Gorsuch |
| 5,984,891 A | 11/1999 | Keilman et al. |
| 5,989,238 A | 11/1999 | Ginsburg |
| 5,989,423 A | 11/1999 | Kamen et al. |
| 6,024,720 A * | 2/2000 | Chandler et al. ............... 604/35 |
| 6,042,784 A | 3/2000 | Wamsiedler et al. |
| 6,069,343 A | 5/2000 | Kolowich |
| 6,074,359 A | 6/2000 | Keshaviah et al. |
| 6,129,699 A | 10/2000 | Haight et al. |
| 6,139,528 A | 10/2000 | Kistner et al. |
| 6,142,974 A | 11/2000 | Kistner et al. |
| 6,146,359 A | 11/2000 | Carr et al. |
| 6,168,578 B1 | 1/2001 | Diamond |
| 6,175,688 B1 | 1/2001 | Cassidy et al. |
| 6,193,684 B1 | 2/2001 | Burbank et al. |
| 6,196,992 B1 | 3/2001 | Keilman et al. |
| 6,210,361 B1 | 4/2001 | Kamen et al. |
| 6,220,299 B1 | 4/2001 | Arvidsson et al. |
| 6,228,047 B1 | 5/2001 | Dadson |
| 6,229,957 B1 | 5/2001 | Baker |

(56) References Cited

U.S. PATENT DOCUMENTS

| | | |
|---|---|---|
| 6,234,991 B1 | 5/2001 | Gorsuch |
| 6,234,992 B1 | 5/2001 | Haight et al. |
| 6,236,809 B1 | 5/2001 | Cassidy et al. |
| 6,245,039 B1 | 6/2001 | Brugger et al. |
| 6,254,567 B1 | 7/2001 | Trea et al. |
| 6,261,261 B1 | 7/2001 | Gordon |
| 6,261,809 B1 | 7/2001 | Bertling et al. |
| 6,290,669 B1 | 9/2001 | Zicherman |
| 6,293,921 B1 | 9/2001 | Shinmoto et al. |
| 6,302,653 B1 | 10/2001 | Bryant et al. |
| 6,319,221 B1 * | 11/2001 | Savage et al. ............ 604/28 |
| 6,579,253 B1 | 6/2003 | Burbank et al. |
| 6,602,502 B1 | 8/2003 | Strahilevitz |
| 6,746,607 B1 | 6/2004 | Vijayalakshmi et al. |
| 6,960,179 B2 | 11/2005 | Gura |
| 7,241,272 B2 | 7/2007 | Karoor et al. |
| 2001/0027289 A1 | 10/2001 | Treu et al. |
| 2001/0037079 A1 | 11/2001 | Burbank et al. |
| 2001/0041892 A1 | 11/2001 | Burbank et al. |
| 2002/0147423 A1 | 10/2002 | Burbank et al. |
| 2002/0187940 A1 | 12/2002 | Masuda et al. |
| 2003/0000876 A1 | 1/2003 | Kawaguchi |
| 2003/0105424 A1 | 6/2003 | Karoor et al. |
| 2005/0101901 A1 | 5/2005 | Gura |
| 2005/0102028 A1 | 5/2005 | Arnin et al. |

FOREIGN PATENT DOCUMENTS

| | | |
|---|---|---|
| EP | 64393 | 11/1982 |
| EP | 152717 | 8/1985 |
| EP | 0243547 | 7/1991 |
| EP | 0402505 | 12/1993 |
| EP | 0498382 | 11/1996 |
| EP | 0778033 | 11/1996 |
| EP | 0575512 | 5/1998 |
| EP | 0928615 | 7/1999 |
| EP | 0956876 | 11/1999 |
| EP | 980685 | 2/2000 |
| EP | 0659092 | 10/2000 |
| EP | 0847769 | 8/2001 |
| GB | 2122509 | 1/1984 |
| GB | 2124511 | 2/1984 |
| JP | 55-32384 | 3/1980 |
| JP | 92002060 | 1/1992 |
| JP | 4348757 | 3/1992 |
| JP | 07-299455 | 11/1995 |
| JP | 8029224 | 2/1996 |
| JP | 96029224 | 2/1996 |
| JP | 9327511 | 12/1997 |
| JP | 10085324 | 4/1998 |
| JP | 11137672 | 5/1999 |
| JP | 200120483 | 12/2000 |
| SE | 1012918 | 3/1981 |
| SE | 1344362 | 6/1984 |
| WO | 4/20158 | 9/1994 |
| WO | 95/02559 | 1/1995 |
| WO | 95/35124 | 12/1995 |
| WO | 97/47337 | 6/1997 |
| WO | 98/17333 | 4/1998 |
| WO | 99/03519 | 1/1999 |
| WO | 99/06082 | 2/1999 |
| WO | 00/20050 | 4/2000 |
| WO | 00/20052 | 4/2000 |
| WO | 00/50143 | 8/2000 |
| WO | 00/57928 | 10/2000 |
| WO | 02/43859 | 6/2002 |

OTHER PUBLICATIONS

Japanese Office Action dated Dec. 14, 2012 for related application No. 2011-100145—1 page,—corresponding communication indicates no references cited in Japanese Office Action.

Japanese Office Action received Jun. 13, 2013 for Japanese Application No. 2011-100145.

* cited by examiner

WEIGHT/SENSOR-CONTROLLED SORBENT SYSTEM FOR HEMODIALYSIS

PRIORITY claim

This application claims priority to and the benefit as a continuation of U.S. patent application Ser. No. 12/562,730, filed Sep. 18, 2009, entitled "Systems And Methods For Performing Peritoneal Dialysis", now U.S. Pat. No. 8,357,113, issued on Jan. 22, 2013, which is a continuation of U.S. patent application Ser. No. 10/623,316, filed Jul. 17, 2003, entitled "Systems And Methods For Performing Peritoneal Dialysis", now U.S. Pat. No. 7,867,214, issued Jan. 11, 2011, which claims priority to and the benefit of U.S. Provisional Patent Application Ser. No. 60/397,131, filed Jul. 19, 2002, entitled "Systems And Methods For Performing Peritoneal Dialysis", the entire contents of each of which are hereby incorporated by reference and relied upon.

BACKGROUND

The present invention generally relates to dialysis systems. More specifically, the present invention relates to regeneration dialysis systems and continuous flow dialysis systems. The present invention also relates to methods of performing dialysis therapies.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis therapies commonly used to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. A large amount of dialysate, for example about 120 liters, is used to dialyze the blood during a single hemodialysis therapy. The spent dialysate is then discarded. Hemodialysis treatment lasts several hours and is generally performed in a treatment center about three or four times per week.

One type of hemodialysis therapy is regenerative hemodialysis. This therapy uses a hemodialysis system, which includes a cartridge for dialysate regeneration. One such cartridge is manufactured under the name REDY™ by Sorb Technology, Oklahoma City, Okla. In this system, the dialysate fluid flow path must be properly cleaned before the hemodialysis machine can be used on another patient. Also, the dialysate fluid flow path is not a closed system, i.e., the dialysate fluid flow path is open to the atmosphere, such that oxygen from the atmosphere can contact fluid in the system and foster the growth of bacteria in same. Consequently, contamination of such a dialysis system can be a concern. Further, the dialysate fluid exiting the REDY™ cartridge is not suitable for peritoneal dialysis because the fluid is relatively acidic and not, therefore, physiologic. Moreover, this system requires the attention of medical personnel during therapy.

Peritoneal dialysis utilizes a sterile, pyrogen free dialysis solution or "dialysate", which is infused into a patient's peritoneal cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated on a semi-continuous or continuous basis.

There are various types of peritoneal dialysis therapies, including continuous ambulatory peritoneal dialysis ("CAPD") and automated peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each exchange or treatment cycle, which includes a drain, fill and dwell, takes about four hours. Manual peritoneal dialysis performed by the patient requires a significant amount of time and effort from the patient. This inconvenient procedure leaves ample room for improvement and therapy enhancements to improve patient quality of life.

Automated peritoneal dialysis is similar to continuous peritoneal dialysis in that the dialysis treatment includes a drain, fill, and dwell cycle. However, a dialysis machine automatically performs three to four cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysate and to a fluid drain. The dialysis machine pumps spent dialysate from the peritoneal cavity, though the catheter, to the drain. The dialysis machine then pumps fresh dialysate from the dialysate source, through the catheter, and into the patient's peritoneal cavity. The automated machine allows the dialysate to dwell within the cavity so that the transfer of waste, toxins and excess water from the patient's bloodstream to the dialysate solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a "last fill" is often used at the end of the automated dialysis treatment, which remains in the peritoneal cavity of the patient when the patient disconnects from the dialysis machine for the day. Automated peritoneal dialysis frees the patient from having to manually performing the drain, dwell, and fill steps. Automated dialysis can improve the patient's dialysis treatment and undoubtedly improves the patient's quality of life.

So-called "continuous flow" peritoneal dialysis ("CFPD") systems that purport to provide continuous dialysate flow exist. However, these systems typically have a single pass fluid flow. That is, the dialysate flows into, through, and out of the peritoneal cavity one time before being sent to a drain. The "spent" dialysate (waste laden dialysate) from the patient collects in a drain bag, which is discarded, or runs into a household drain or other drain. Known CFPD systems, therefore, typically use a volume of disalysate one time and then discard it. That is, the systems have no ability to regenerate or reuse a quantity of dialysate.

The effectiveness of existing peritoneal dialysis therapies, and existing systems which perform the therapies, depends upon the amount of dialysis fluid used. For example, typical peritoneal dialysis therapy requires about 4 to 6 exchanges of dialysate (drain, fill, dwell) with about 2 to 3 liters of dialysate for each exchange. Peritoneal dialysis is a daily therapy performed 7 days per week. As a consequence, 240 to 540 liters of fresh dialysate must be delivered to and stored at a patient's home each month. Increasing dialysate dosage to increase therapy effectiveness will necessitate even more dialysate.

Therefore, needs exist to provide improved dialysis systems and methods of performing dialysis. Particularly, needs exist to provide closed loop peritoneal dialysis systems and methods that regenerate or reuse spent dialysate. There are needs for such systems and methods to be compatible with CFPD treatment so that patients can perform the procedure at home without the need for storing an inordinate amount of fresh dialysate bags. There are further needs for such systems and methods to be automated so that the procedure can be largely performed at night while the patient sleeps.

SUMMARY

Generally, the present invention provides improved dialysis systems and improved methods of performing dialysis. More particularly, the present invention provides systems and methods for continuous flow dialysis ("CFD") and regenerative dialysis, and in combination, continuous flow regenerative dialysis ("CFRD"). This invention also includes improved systems and methods for performing hemodialysis.

The dialysis system of the present invention automatically performs dialysis therapy on a patient, for example, during nighttime while the patient sleeps. The present invention automatically regenerates spent dialysate into fresh dialysate that is reintroduced into the patient to be used again for dialysis treatment. Further, the dialysis system provides continuous fluid flow simultaneously to and from the patient.

To this end, in one embodiment of the present invention a system for providing dialysis is provided. The system includes a patient fluid loop having a first pump and multiple patient lumens. The system includes a second fluid loop including a second pump and a medical fluid regenerator. A membrane device is placed in fluid contact with and separates the patient and the second fluid loops. The membrane device allows at least one selected component of the fluid in the patient fluid loop to transfer to the second fluid loop. The second loop is otherwise closed except for the transfer of the selected component via the membrane device. A controller is also provided that operates the first and second pumps to recirculate fluid in the patient loop and the second loop.

The system is adaptable to be used with various different types of components and to be arranged in a variety of ways.

For example, in an embodiment, the membrane device is a dialyzer.

In an embodiment, a pressure gradient exists across the membrane device.

In an embodiment, the patient loop is also closed except for the transfer of the selected component via the membrane device and the venting of air/gas.

In an embodiment, the membrane device includes a nanofilter which allows urea to pass from the patient fluid loop to the second fluid loop.

In an embodiment, the medical fluid regenerator includes a uremic toxin sorbent.

In an embodiment, the medical fluid regenerator can include any or all of the following materials: urease, zirconium phosphate, zirconium oxide, and carbon.

In an embodiment, the system includes a gas separator that removes gas from one or both of the patient and second fluid loops.

In an embodiment, the gas separator and the medical fluid regenerator are provided in a single device.

In an embodiment, the system includes a gas vent that vents gases from the patient and second fluid loops.

In an embodiment, the second fluid loop includes a multianalyte sensor that monitors a concentration of electrolytes in the medical fluid.

In an embodiment, peritoneal dialysis fluid is circulated through the patient fluid loop.

In an embodiment, blood is circulated through the patient fluid loop.

In an embodiment, at least parts of the patient fluid loop and the second fluid loop are provided in a disposable device.

In an embodiment, the second fluid loop includes a balance chamber that balances flow within the second fluid loop.

In an embodiment, the controller enables fluid to flow in opposite directions through the multiple patient.

In an embodiment, the system includes a dual lumen catheter that defines the multiple patient lumens.

In an embodiment, one or both of the patient fluid loop and the second fluid loop includes an in-line fluid heater.

In an embodiment, the in-line fluid heater includes a radiant heater and a plate heater.

In an embodiment, the system includes a medical fluid sensor which senses one or more indicators including: ammonia, ammonium and pH.

In an embodiment, the system includes a fluid volume sensor in or both of the patient and second fluid loops.

In an embodiment, the fluid volume sensor includes a capacitance fluid volume sensor that uses a chamber in fluid communication with one or both of the fluid loops.

In an embodiment, the chamber is a pump chamber.

In an embodiment, the system includes an ultrafiltrate container in fluid communication with at least one of the patient and second fluid loops.

In an embodiment, the system includes a fluid concentrate container in fluid communication with one or both of the patient and second fluid loops.

The system as described herein uses, in one embodiment, a disposable dialysis cassette. The cassette includes a flexible membrane covering a patient pump chamber and a regeneration pump chamber. The cassette includes an apparatus for fluidly connecting the patient pump chamber to a closed loop patient fluid path. The cassette further includes an apparatus for fluidly connecting the regeneration pump chamber to a closed loop regeneration fluid path. The patient path and the regeneration path each fluidly communicates with a dialyzer.

The cassette is adaptable to be used with various different types of components and to be arranged in a variety of ways.

For example, in an embodiment, the disposable cassette defines a fluid path leading to a port that fluidly communicates with a dialysate sorbent cartridge.

In an embodiment, the disposable cassette defines a fluid path leading to a port that fluidly communicates with a gas separator.

In an embodiment, the disposable cassette defines a fluid path leading to a port that fluidly communicates with a dialysis concentrate container.

In an embodiment, the disposable cassette defines a fluid path leading to a port that fluidly communicates with a dialysate last bag.

In an embodiment, the disposable cassette defines a fluid path leading to a port that fluidly communicates with a dialysate bag.

In an embodiment, the disposable cassette defines a fluid path leading to a port that fluidly communicates with a drain container.

In an embodiment, the disposable cassette defines a fluid path leading to a port that fluidly communicates with a patient fluid connector.

Further, the disposable cassette can define a fluid path for a twenty-four hour collection and/or a remote analyte sensor.

The disposable cassette operates with a dialysis therapy device. The therapy device includes a housing having a portion that receives the disposable cassette. The housing houses a patient pump actuator that pumps fluid through a patient path defined at least in part by the disposable cassette. The housing also houses a regeneration pump actuator that pumps fluid through a regeneration path defined at least in part by the disposable cassette.

The dialysis therapy device is also adaptable to be used with various different types of components and to be arranged in a variety of ways.

For example, in an embodiment, the dialysis therapy device includes at least one fluid volume measurement sensor component that cooperates with the patient pump actuator and the regeneration pump actuator.

In an embodiment, the housing houses a fluid heater.

In an embodiment, the housing houses at least one sensor, such as an ammonia sensor, an ammonium sensor and a pH sensor.

In an embodiment, the housing houses at least one valve actuator that operates with the disposable cassette.

The present invention includes a plurality of different methods for operating the systems and apparatuses described herein. In one embodiment, a method is provided for moving fluid in a dialysis system. The method includes continuously recirculating a first fluid through a patient loop. The method includes continuously recirculating a second fluid through a regeneration loop. At least one waste component is simultaneously transferred from the patient loop to the regeneration loop through a device shared by both loops. The loops are otherwise closed except for the fluid transfer through the device. The method also includes removing the at least one waste component from the regeneration loop.

The first and second fluids can both include dialysate. Alternatively, the first fluid includes blood and the second fluid includes dialysate.

In an embodiment, the method includes flowing the second fluid in the regeneration loop through a waste sorbent and absorbing at least some of the waste component.

In an embodiment, the method includes the step of heating the at least one of the first and second fluids.

In an embodiment, the method includes the step of removing ultrafiltrate from at least one of the first and second fluids.

In an embodiment, the method includes the step of adding dialysate to at least one of the first and second fluids.

In an embodiment, the method includes the step of adding concentrate to at least one of the first and second fluids.

In an embodiment, the method includes the step of removing gas from at least one of the first and second fluids.

In an embodiment, the method includes the step of balancing the flow of fluid in at least one of the patient loop and the regeneration loop.

In an embodiment, the method includes the step of sensing a volume of flow of fluid in at least one of the patient loop and the regeneration loop.

In an embodiment of any of the methods described herein, recirculating dialysate fluid through the patient loop includes passing the fluid through a portion of a patient.

In an embodiment, the method is for continuous flow peritoneal dialysis and includes passing the dialysate fluid and the regeneration fluid past opposite sides of a dialyzer membrane and regenerating the regeneration fluid after the regeneration fluid exits the dialyzer.

In an embodiment of the continuous flow peritoneal dialysis method, recirculating dialysate fluid through the closed patient loop includes passing the fluid through a sleeping patient.

In an embodiment of the continuous flow peritoneal dialysis method, recirculating dialysate fluid through the closed patient loop includes passing the fluid through a patient at nighttime.

In another embodiment, a method of moving fluid in a peritoneal dialysis system is provided. The peritoneal dialysis method includes the steps of: (i) continuously recirculating dialysate through a container in a patient loop: (ii) continuously recirculating dialysate through the container in a regeneration loop; and (iii) continuously moving at least one waste component from the patient loop to the regeneration loop through the container shared by both loops, the loops being closed except for said transfer through said container.

In an embodiment, the peritoneal dialysis method includes the step of recirculating dialysate through the regeneration loop at a different rate than a rate at which dialysate is recirculated through the patient loop.

In a further method of the present invention, performing continuous flow dialysis includes multiple dialysis disciplines. The method includes performing continuous flow peritoneal dialysis with a closed loop dialysis device at a first point in time and performing continuous flow hemodialysis via the same closed loop dialysis device at a second point in time.

In an embodiment, the continuous flow peritoneal dialysis and the continuous flow hemodialysis are performed on the same patient.

In an embodiment, the method includes an intermediate step of removing a disposable cassette used with the device and coupling a new disposable cassette to the device.

In an embodiment, the method includes an intermediate step of removing a dual lumen peritoneal dialysis catheter and replacing the catheter with a hemodialysis needle.

In an embodiment, the method includes an intermediate step of removing a hemodialysis needle and replacing the needle with a dual lumen peritoneal dialysis catheter.

One advantage of the present invention is to provide improved systems and methods for performing dialysis.

Another advantage of the present invention is to provide improved systems and methods for performing automated continuous flow dialysis systems and methods.

A further advantage of the present invention is to provide regenerative dialysis systems and methods of operating same.

Still another advantage of the present invention is to provide a regenerative dialysis system that has clinical advantages.

Still a further advantage of the present invention is to provide a regenerative dialysis system that has economic advantages.

Yet another advantage of the present invention is to provide a regenerative dialysis system that has quality of life advantages.

Still further, an advantage of the present invention is to provide a regenerative dialysis system that reduces the amount of dialysis fluid need to perform dialysis.

Another advantage of the present invention is to provide a closed loop dialysis system.

Other advantages of the present invention are to provide systems and methods for performing both peritoneal dialysis and hemodialysis.

Additional features and advantages of the present invention are described in, and will be apparent from, the following Detailed Description of the Invention and the figures.

DETAILED DESCRIPTION

Figure 1:
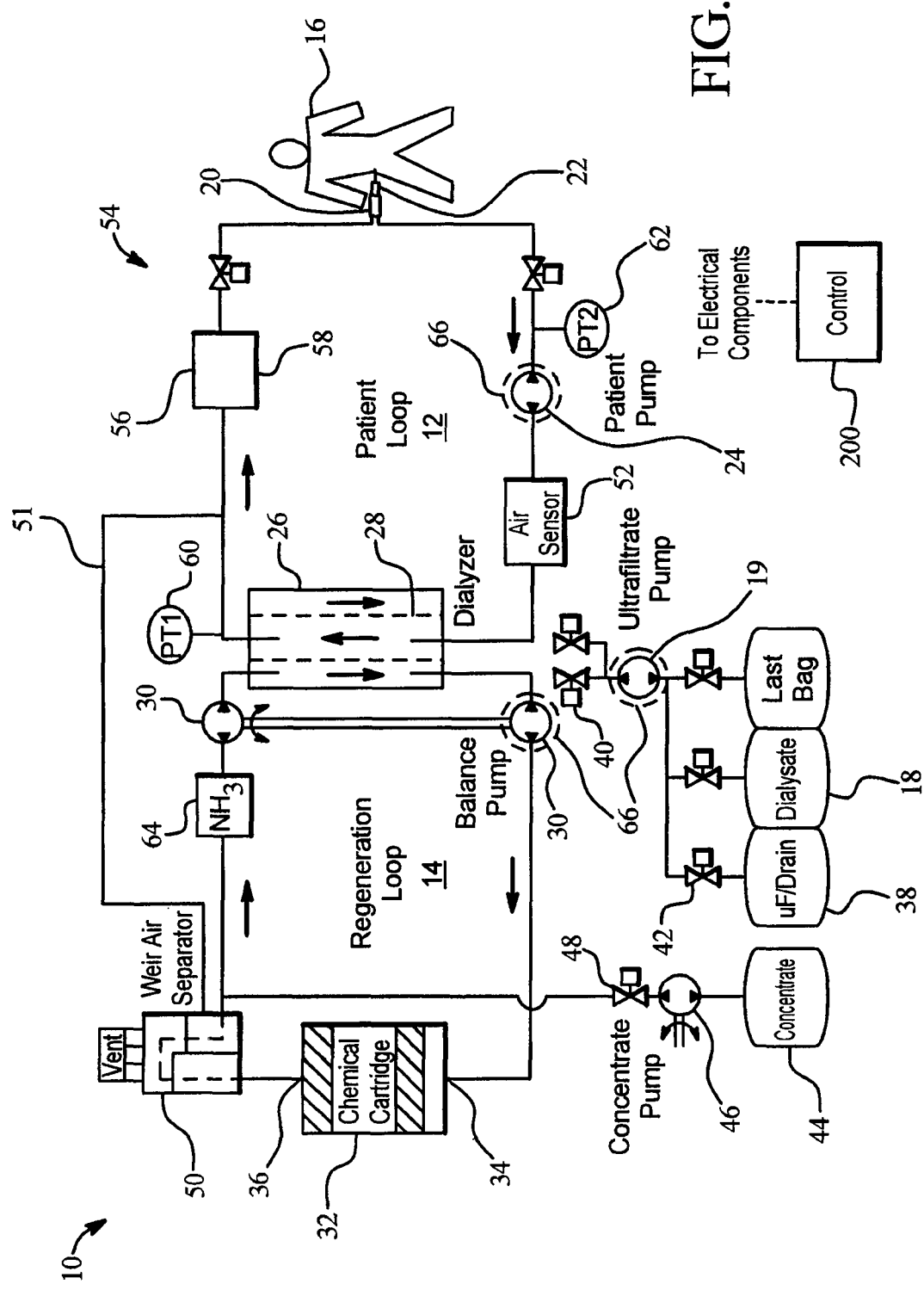
FIG. 1 schematically illustrates an embodiment of a dialysis system according to the principles of the present invention.

Generally, the present invention relates to dialysis systems and methods of performing dialysis. In an embodiment, the present invention pertains to continuous flow regeneration peritoneal dialysis systems and methods. In other embodiments the present invention pertains to non-continuous flow regeneration peritoneal dialysis, and regeneration hemodialysis, both continuous and non-continuous flow.

The dialysis system automatically performs dialysis therapy on a patient, for example during nighttime while the patient sleeps. The present invention can provide true continuous flow dialysis therapy (fluid simultaneously flowing into and out of the patient), and automatically regenerate spent dialysate into fresh dialysate that is again used for the dialysis treatment. Continuous flow of dialysate tends to increase the efficacy of treatment by maximizing or maintaining a maximum osmotic gradient across the peritoneal membrane. Regeneration of dialysate by the present invention significantly reduces the amount of dialysate required for a treatment. For example, the amount of dialysate fluid can be reduced from about fifty liters for CFPD therapy if performed by an existing cycler to about six to eight liters of same for therapy with the present invention.

In a peritoneal dialysis embodiment of the present invention, the spent dialysate from the patient's peritoneal cavity passes through a regeneration unit and is regenerated into a useable dialysate. The regenerated dialysate in a patient fluid loop is returned to the patient's peritoneal cavity to further dialyze the patient. The regeneration unit removes undesirable components in the dialysate that were removed from the patient, for example, excess water (ultrafiltrate or UF), toxins, and metabolic wastes, so that the dialysate can be used for further dialysis. Desirable components can be added to the dialysate by the system, such as glucose and electrolytes, for example. The additives assist in maintaining the proper osmotic gradients in the patient to perform dialysis and provide the necessary compounds to the patient.

Continuous flow peritoneal dialysis according to the present invention means that when the patient is being dialyzed (e.g., dialysate is being pumped to and removed from the peritoneal cavity), the dialysate is constantly and simultaneously flowing into and out of the patient. The dialysis system pumps fresh dialysate into the patient's peritoneal cavity while simultaneously pumping spent dialysate out of the peritoneal cavity. Accordingly, the dialysis system can eliminate the dwell period inside the peritoneal cavity that is typical for existing dialysis systems. The flow rate of the continuous dialysate flow can be constant or varied as desired, and is generally about 100-300 ml/min.

The dialysis system of the present invention can be controlled to provide various dialysis therapies, as desired. Accordingly, even though the dialysis system can provide continuous flow, the present invention also supports non-continuous flow or batch systems and methods. Also, the continuous flow into and out of the peritoneal cavity occurs during the main therapy treatment, so that a dwell during a last bag, for example, does not detract from the continuous flow feature. Furthermore, the fluid pumping mechanisms of the present invention may provide for brief intermittent fluid flow, such as the filling of a pump chamber, for example. The continuous fluid flow of the present invention is considered to include such brief intermittent fluid flow.

The dialysis systems and methods of the present invention provide advantages compared to other dialysis systems and therapies, such as clinical advantages, economic advantages, and quality of life advantages, for example. It is believed that the present invention has clinical advantages, such as, improved blood pressure ("BP") control, improved hematocrit ("HCT") control, improved fluid volume control, improved preservation of residual renal function ("RRF"), improved adequacy vs. the National Kidney Foundation's DOQI standard, higher efficiency (clearances/time), lower glucose absorption, glucose profiling and ultrafiltrate management, and reduced catheter channeling.

It is also believed that the present invention has economic advantages, such as, reduced therapy cost and reduced Epogen ("EPO") usage. Further, it is believed that present invention has quality of life advantages, such as, increased awake time free from dialysis devices, improved patient access, reduced complexity, reduced self-administration of drugs, reduced therapy training, elimination of the need for having a home water infrastructure, a reduced amount of fluid that the patient must handle and manage, simpler prescriptions and elimination of patient transportation to dialysis centers.

The dialysis systems and methods of the present invention more closely simulate and replace continuous kidney functioning as compared to intermittent dialysis therapies. This, in turn, can contribute to improved clinical outcomes (RRF, HCT, BP, for example) while minimally impacting the patient's lifestyle. The efficiency and convenience of the present invention provides patients with a renal replacement therapy that is relatively unrestrictive. This allows patients to have greater freedom from limitations experienced by dialysis devices and therapies. The present invention can provide easier entrance into early dialysis therapy because the system can enable the physician to retain a patient's RRF while minimally impacting the patient's lifestyle.

Dual Loop System

Referring now to the drawings and in particular to FIG. 1, a system 10 for providing dialysis treatment to a patient needing same is illustrated. As illustrated in FIG. 1, two loops are provided: a patient loop (a recirculating patient fluid flow path) 12 and a regeneration loop 14 (a recirculating dialysate fluid flow path). However, it should be noted that the present invention can be used in a system including only one loop or more than two loops. The patient loop 12 is used to dialyze the patient 16 with dialysate in a peritoneal dialysis embodiment. The regeneration loop 14 also contains dialysate and is used to regenerate the dialysate in the patient loop 12. In a hemodialysis embodiment, the patient loop 12 carries the patient's blood, and the regeneration loop 14 dialyzes the blood and regenerates the dialysate in the loop 14.

As illustrated generally in FIG. 1, the patient loop 12 and the regeneration loop 14 are initially filled or primed with dialysate fluid from a bag 18 by pumping the dialysate through a pump, such as an ultrafiltrate pump 19. FIG. 1 shows a single dialysate bag 18 for both the patient and regeneration loops 12 and 14; however, separate dialysate bags and/or fluid pumps could be individually used for the patient loop 12 and the regeneration loop 14. In a hemodialysis embodiment, the patient loop 12 can be primed with a suitable priming solution, such as a saline solution, and then connected to the patient's blood circulatory system.

Figure 2:
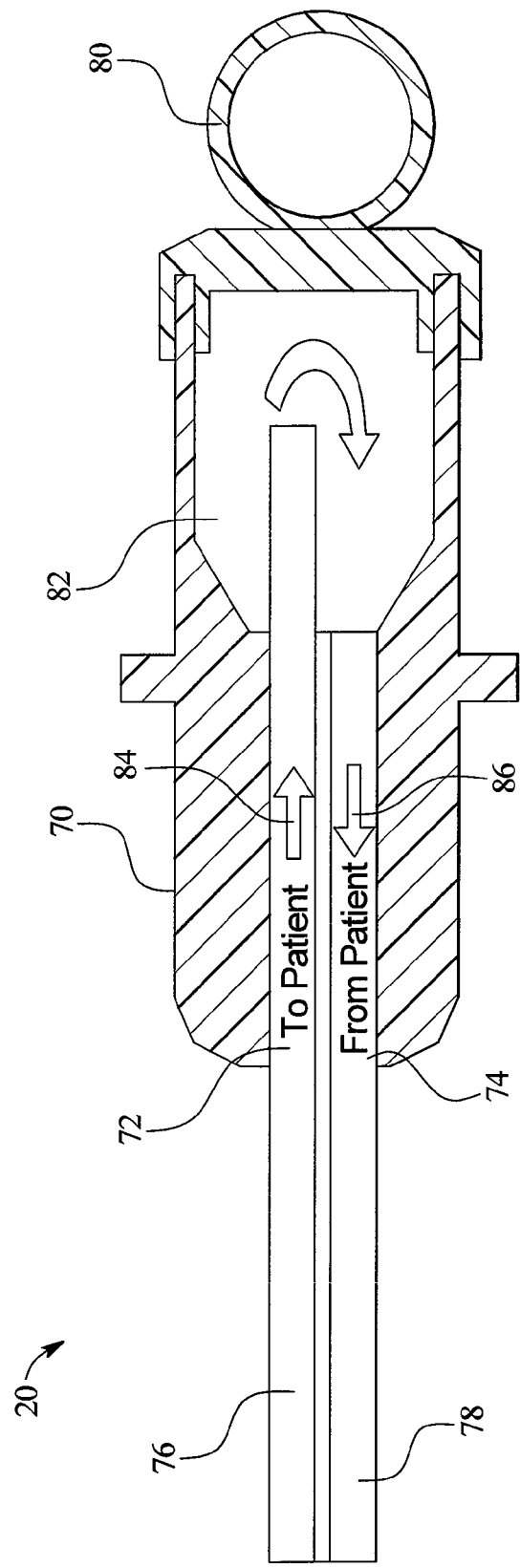
FIG. 2 shows a multi-lumen patient fluid connector according to the principles of the present invention.

The patient loop 12 is fluidly connected to the patient 16 by a multi-lumen patient fluid connector 20 and catheter. Referring to FIGS. 1 and 2, the multi-lumen patient fluid connector 20 can have, for example, a single housing 70 having more than one separate lumen 72 (to patient lumen) and 74 (from patient lumen), or separate housings each having one of the lumens 72 and 74. In a peritoneal dialysis embodiment, the multi-lumen patient fluid connector 20 can be connected to a dual lumen catheter 22 (illustrated in FIG. 1), such as a catheter disclosed in U.S. patent application Ser. No. 09/689,508, titled "Peritoneal Dialysis Catheters," now U.S. Pat. No. 6,976,973, incorporated by reference or other multi-fluid path patient access.

The dual lumen catheter 22 is implanted in the patient 16 and provides fluid flow access to the patient's peritoneal cavity. Two separate lumens 72 and 74 of the multi-lumen patient connector 20 are fluidly connected to separate lumens (not illustrated) of the dual lumen catheter 22. Fluid in the patient loop 12 can continuously flow through the patient fluid connector 20 simultaneously and continuously in multiple directions, e.g. two different directions, into and out of the catheter 22 and the patient 16. The multi-lumen patient fluid connector 20 is described in further detail below in FIG. 2.

In a continuous flow embodiment, the patient loop 12 can be fluidly connected to the patient by any device or devices that provides for fluid to simultaneously flow into and out of the patient. For example, the patient loop 12 can be connected to the dual lumen catheter to two single lumen catheters.

In FIG. 1, the patient loop 12 has a patient fluid pump 24 that pumps fluid through the patient loop 12. The fluid in the patient loop 12 is pumped from the patient 16 (the patient's peritoneal cavity in a peritoneal dialysis embodiment) through the patient fluid connector 20, through a dialyzer 26, back through the patient fluid connector 20, and is returned to the patient 16. In a peritoneal dialysis embodiment, the spent dialysate (laden with waste and excess water) in the patient loop 12 exiting from the patient 16 is cleansed or regenerated by passing through the dialyzer 26. The waste, such as urea, creatinine and excess water passes from the patient loop 12 across a dialyzer membrane 28 to the regeneration loop 14 to produce fresh dialysate exiting the dialyzer in the patient loop 12. The fresh dialysate is returned to the patient 16 for further dialysis treatment. In an embodiment, the fluid in the patient loop 12 is continuously recirculated through the patient loop 12 by the patient pump 24. Also, the dialyzer 26 provides a sterile independent barrier between the patient loop 12 and the regeneration loop 14. Existing dialyzers used for dialysis is therapy are suitable for use with the present invention, for example. Also, the membrane 28 referred to in the dialyzer 26 includes any suitable filter material, such as hollow dialyzer fibers.

In a hemodialysis embodiment, the patient loop 12 is connected to the patient's blood circuit rather than the peritoneal cavity. The patient pump 24 continuously recirculates the blood, as the dialyzer 26 removes waste and excess from the blood.

The regeneration loop 14 removes the waste and excess water from the patient loop 12. In the embodiment illustrated in FIG. 1, a fluid pump 30, pumps dialysate fluid in the regeneration loop 14 continuously to recirculate the dialysate through the loop 14. The dialysate fluid pump 30 pumps the dialysate from the dialyzer 26, through a sorbent cartridge 32, and back to the dialyzer 26. The fluid in the regeneration loop 14 flows past a side of the dialyzer membrane 28 opposite the side of the membrane 28 having the fluid in the patient loop 12. In an embodiment, the regeneration loop 14 provides for balanced fluid flow through the dialyzer 26, for example, by providing equal flow dialysate fluid pumps 30, and/or balance chambers.

As mentioned above, waste and excess water passes from the fluid in the patient loop 12, across the dialyzer membrane 28, to the fluid in the regeneration loop 14. The transfer across the dialyzer membrane 28 occurs at least in part due to diffusion and concentration gradients across the membrane 28. Also, the system 10 in an embodiment maintains a lower fluid pressure in the regeneration loop 14 relative to the patient loop 12. That is, there is a transmembrane pressure ("TMP") across the dialyzer membrane 28. The fluid pressure differential draws fluid from the patient loop 12, across the dialyzer membrane 28, to the regeneration loop 14. This fluid pressure differential can be maintained by removing fluid from the regeneration loop 14, for instance, by using the ultrafiltrate pump 19 to drain some of the fluid in the regeneration loop 14. The amount or rate of fluid removed from the regeneration loop 14 by the ultrafiltrate pump 19 determines the amount or rate of fluid transferring from the patient loop 12, across the dialyzer membrane 28, to the regeneration loop 14. This amount or rate equals the amount or rate of fluid removed from the patient 16 to the patient loop 12.

A sorbent cartridge or container 32 includes materials that absorb particular compounds from the dialysate. For example, certain sorbents within the sorbent cartridge 32 may absorb uremic toxins, such as urea, creatinine, uric acid, and other metabolism by-products. By removing these undesirable waste materials, the sorbent cartridge 32 at least partially regenerates the dialysate. The sorbent cartridge 32 includes a body having a fluid inlet 34 and a fluid outlet 36. One sorbent cartridge 32 according to the invention contains four layers of materials, including a first layer of urease, a second layer of zirconium phosphate, a third layer of zirconium oxide and a fourth layer of carbon. The interior of the cartridge 32 is constructed and arranged so that the fluid entering the interior from the inlet 34 flows (preferably upward and uniformly) through the first layer, the second layer, the third layer, the fourth layer and finally through the outlet 36.

The sorbent cartridge 32 can also use materials that selectively remove certain solutes from the dialysate. The selective materials can include a binder or reactive sorbent material capable of selectively removing urea, a binder or reactive sorbent material capable of selectively removing phosphate and/or the like. The use of materials capable of selective removal of solutes, particularly urea, enhances the cleaning efficiency of the system of the present invention such that the amount of dialysate necessary for effective treatment can be minimized.

The materials that can selectively remove solutes from solution, such as binder materials, can include a variety of suitable and different materials including, for example, polymeric materials that are capable of removing nitrogen-containing compounds, such as urea, creatinine, other like metabolic waste and/or the like in solution. In general, these types of materials contain a functional group(s) that chemically binds with urea or other like solutes.

For example, U.S. Pat. Nos. 3,933,753 and 4,012,317, each incorporated herein by reference, disclose alkenylaromatic polymers containing phenylglyoxal that can function to chemically bind urea. In general, the phenylglyoxal polymeric material is made via acetylation performed in, for example, nitrobenzene followed by halogenation of the acetyl group and treatment with dimethylsulfoxide as disclosed in U.S. Pat. Nos. 3,933,753 and 4,012,317. Another example of a polymeric material that is capable of selectively removing solutes, such as urea, from solution includes polymeric materials that contain a tricarbonyl functionality commonly known as ninhydrin as disclosed in U.S. Pat. No. 4,897,200, incorporated herein by reference. However, it should be appreciated that the present invention can include any suitable type of material or combinations thereof to selectively remove solutes, such as urea, from solution as previously discussed.

In addition to absorbing certain materials from the dialysate, the sorbent cartridge 32 may also modify the dialysate in the regeneration loop 14 in other ways. For example, the materials in the sorbent cartridge 32 mentioned above or additional materials added to the cartridge 32 may modify the pH of the fluid passing through the cartridge 32. In an embodiment, the pH of the dialysate in the regeneration loop 14 is modified as needed to maintain a physiologic level. One sorbent cartridge 32 is described in further detail in a U.S. patent application titled "Method and Composition for Removing Uremic Toxins in Dialysis Processes," Ser. No. 09/990,673, now U.S. Pat. No. 7,241,272, incorporated herein by reference.

The sorbent cartridge 32 can also include a number of components in addition to the sorbent materials capable of removing solutes from the dialysate. For example, the cleaning cartridge may have the capability to remove all or a portion of electrolytes, such as sodium, potassium, or the like, from the dialysate solution. In this case, an additional source of electrolytes in solution may be needed to replenish the dialysate after it has been cleaned. The cartridge may also be configured to release bicarbonate or the like into the system depending on the type of sorbent material used. This can facilitate pH regulation of the dialysate. As necessary, the cartridge may be filtered to prevent proteins, particulate matter or like constituents from leaching or exiting from the cartridge and into the dialysate.

Ultrafiltrate (excess water) removed from the patient 16 can be removed from the dialysis system 10 by draining the ultrafiltrate to a drain bag 38 or other drain means. In one embodiment, the ultrafiltrate pump 19 removes fluid from the regeneration loop 14 at the exit end of the dialyzer 26 through valves 40 and 42 to the drain bag 38, wherein the fluid contains the waste and excess water removed from the patient loop 12 by the dialyzer 26. The drain pump 19 can remove fluid from the regeneration loop 14 continuously or intermittently (e.g., batch operation), as desired.

The dialysis solution in the regeneration loop 14 is removed from the system along with the ultrafiltrate. Accordingly, a dialysate concentrate is provided in a concentrate container 44 to supply necessary compounds to the regeneration loop 14. The concentrate from the container 44 mixes with the dialysate in the regeneration loop 14 and adds the compounds to the dialysate. The concentrate in an embodiment also includes other components that are provided to the patient 16, for example, electrolytes. A concentrate pump 46 and a valve 48 are provided to selectively pump the concentrate from the concentrate container 44 to the regeneration loop 14. The concentrate contributes to the regeneration of the dialysis solution in the regeneration loop 14.

Although the fluids in both the patient loop 12 and the regeneration loop 14 are, in an embodiment, recirculated continuously through their respective loops, the various fluid pumps can be controlled by a computer, processor, or microprocessor, collectively referred to herein as a "controller" 200, to pump their respective fluids intermittently, if desired.

The dialysis system 10 in an embodiment is a closed, sterile system. Air, moisture and fluids from the environment around the dialysis system 10 cannot enter into the patient loop 12 or the regeneration loop 14. The dialysis system 10 does permit fluids (such as ultrafiltrate) and air to exit the fluid loops 12, 14 and fluids (such as concentrate) to be added to the fluid loops 12, 14 under controlled circumstances. The dialysis system 10 is designed to prevent uncontrolled contact of the patient and the regeneration loops 12 and 14 with the surrounding environment.

FIG. 1 schematically shows an example of an gas separator 50 in the dialysis system 10. The term "gas" is used herein to include gasses in general, including air, carbon dioxide ("CO2") and any other type of gas that can become entrained in fluid loops 12 and 14. The regeneration fluid loops 12 and 14 can accumulate air for various reasons. For example, the fluid loops 12 and 14 may contain air prior to priming the system 10 with fluid or the storage containers may introduce air into the fluid loops 12 and 14. The sorbent cartridge 32 may produce CO2 and introduce the CO2 gas into the loops 12 and 14. The patient 16 can also produce certain gasses, which become entrained in the dialysate and enter the loops 12 and 14.

It is desirable to remove gas from the fluid loops 12 and 14. The gas separator 50 removes entrained gas from the fluid in the regeneration loop 14 and vents the gas to outside of the dialysis system 10. In this manner, gas is purged from the regeneration loop 14. The gas separator 50 includes a one-way vent, i.e., it permits gas to vent from the fluid loops 12 and 14 to the atmosphere but prevents gas outside of the fluid loops 12 and 14 from entering into the loops.

Figure 3:
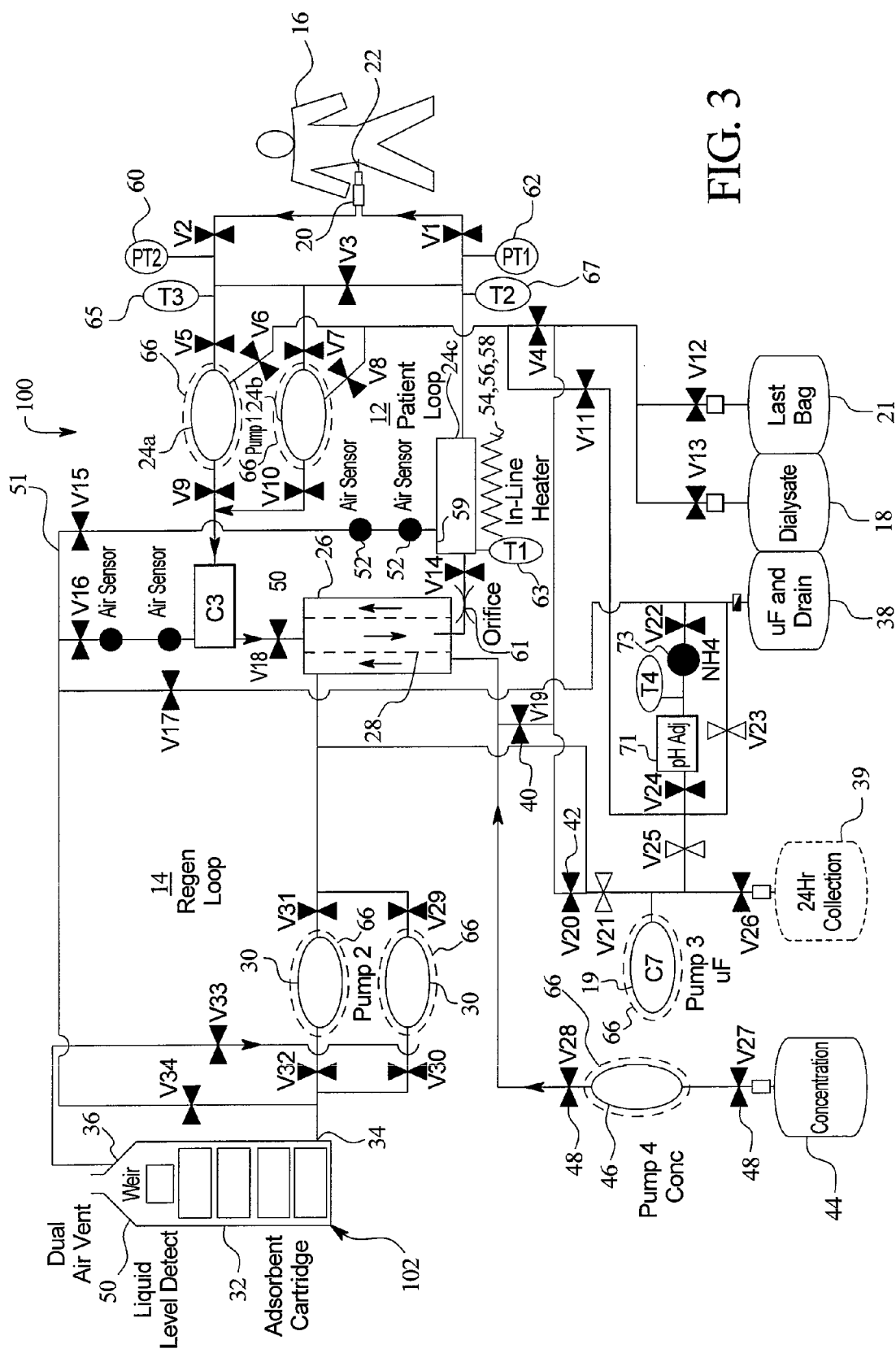
FIG. 3 schematically illustrates another embodiment of a dialysis system according to the principles of the present invention.

In one embodiment illustrated in FIG. 3, the gas separator 50 and the sorbent cartridge 32 of FIG. 1 are combined into a single device 102. One example of a gas separator 50/sorbent cartridge 32 combination is shown in the patent application titled "Method and Composition for Removing Uremic Toxins in Dialysis Processes," Ser. No. 09/990,673, now U.S. Pat. No. 7,241,272, mentioned above. As illustrated in FIG. 1, however, the gas separator 50 can be a separate system component or incorporated into system components other than the sorbent cartridge 32.

It is also desirable to purge gas from the patient loop 12. In an embodiment, an additional gas separator (not illustrated) can be provided in the patient loop 12, which vents to the atmosphere. In another embodiment, the gas can be removed from the patient loop 12, fed to the gas separator 50 in the regeneration loop 14, e.g., via line 51, and vented to the atmosphere.

In an embodiment, one or more gas sensor(s) 52 are provided at desired locations along the patient loop and/or the regeneration loop 14 to detect gas in the system 10. In an embodiment, gas sensors 52 electrically connect or are otherwise in communication with the system controller, which monitors gas content in the loops 12 and 14. The controller can control the system to perform any desired function in response to the gas, such as, stopping fluid flow, changing the direction of fluid flow, or removing the gas. The gas separator 50 can be any suitable device, which separates gas from fluid known to those of skill in the art. Gas separators, such as the separator 50, can be used which separate and vent the gas without being controlled by the system controller. In an embodiment, the gas separator 50 absorbs the gas rather than venting it to the atmosphere as illustrated.

In an embodiment, the dialysis system 10 contains a fluid heater 54, shown schematically in FIG. 1. The fluid heater 54 heats the fluid in the patient loop 12 to a desired temperature for supplying the fluid to the patient 16. The fluid heater 54 is an in-line heater (continuous flow heater) that heats the fluid to the desired temperature as the fluid flows continuously past the heater 54. In other embodiments, heaters other than in-line heaters can be used, for example, bulk heaters. The fluid heater 54 is shown in FIG. 1 in the patient loop 12 at the fluid supply to the patient 16. However, the fluid heater 54 can be positioned at other locations in the patient loop 12 and the regeneration loop 14, if desired. In another embodiment, one or both of the loops 12 and 14 include one or multiple heaters 54.

In an embodiment, the fluid heater 54 is a dual heater, including an infrared heater 56 and a plate heater 58. An example of such a dual heater 54 is disclosed in a patent application entitled. "Medical Fluid Heater Using Radiant Energy," Ser. No. 10/051,609, now U.S. Pat. No. 7,153,285, incorporated herein by reference. Both the infrared heater 56 and the plate heater 58 are in-line heaters that heat the medical fluid that flows continuously past the heaters 56, 58. The radiant energy or infrared heater 56 emits infrared energy that is directed to and absorbed by the fluid in the patient loop 12, thereby heating the fluid. The radiant energy or infrared heater 56 is a primary or high capacity heater which can heat a relatively large volume of cold fluid to a desired temperature in a short period of time.

The plate heater 58 is a secondary or maintenance heater which has a relatively lower heating capacity relative to the infrared heater 56. The plate heater 58 uses electrical resistance to increase the temperature of a plate that in turn heats the fluid flowing near the plate.

The heater 54, which includes both high and low capacity heaters, provides an efficient heater design that accommodates various fluid heating requirements. For example, the radiant or infrared heater 56 is particularly useful for quickly heating cool dialysate (high heat energy demand) that is supplied to the dialysis system 10, such as at the initial system fill or if there is severe heat loss during dialysis treatment. The temperature of the dialysate at initial system fill can be quite low, such as 5° C. to 10° C. if the fluid is stored in cold ambient temperature.

The plate heater 58 is particularly useful to maintain a desired temperature (lower heat energy demand) of the fluid being supplied to the patient, e.g., due to a normal amount of heat loss during dialysis treatment. The infrared heater 56 provides for the high heat demand in a small amount of fluid exposure space, while the plate heater 58 provides for maintenance heat demand and requires a lesser amount of input energy compared to the infrared or radiant heater 56. Furthermore, the heating capacity of the heater 54 is increased if both the infrared and plate heaters 56 and 58 are used together to heat the fluid.

The infrared heater 56 and the plate heater 58 can be arranged in various configurations relative to each other. The heaters 56 and 58 in an embodiment are arranged so that the fluid passes by the heaters sequentially (e.g., first the radiant or infrared heater and then the plate heater). In another embodiment, the fluid passes by the heaters simultaneously (both heaters at the same time) or in the reverse order. The fluid flow path past the heaters 56 and 58 can be a common flow path for both heaters 56 and 58 or include independent flow paths for each heater 56 and 58. Besides radiant or infrared electrical resistance heating, other types of heating such as convective, inductive, microwave and radio frequency ("RF") heating may be used.

In an embodiment, temperature sensors are provided at desired locations along one or both of the patient loop 12 and the regeneration loop 14. The temperature sensors monitor various fluid temperatures and are connected to the system controller to control the fluid temperatures with the heater 54. When two or More heaters, such as the infrared heater 56 and the plate heater 58, are provided in the dialysis system 10, the system 10, in an embodiment, can include separate temperature sensors for each heater so that each heater can be controlled individually.

The dialysis system 10 in an embodiment also includes various other sensors to monitor various parameters. For example, fluid pressure sensors 60 and 62 are provided in the patient loop 12 of FIG. 1. The fluid pressure sensors 60 and 62 electrically couple to or otherwise communicate with the controller to provide a signal that indicates the respective fluid pressure at that location. Based on the signals from the pressure sensors 60 and 62, the controller operates the fluid pumps and valves to obtain and maintain desired fluid pressures in the loop 12 running to and from the patient 16.

In an embodiment, the pressure sensors 60 and 62 are non-invasive pressure sensors. That is, the pressure sensors 60 and 62 do not physically contact (and possibly contaminate) the medical fluid or dialysate. The pressure sensors 60 and 62 measure the medical fluid pressure and help to maintain a steady flow within the closed fluid system. Of course, other fluid devices, such as flow rate sensors, pressure gauges, flowmeters, or pressure regulators, which are not illustrated FIG. 1, may be provided in any suitable quantity and at any desired location within either or both of the patient loop 12 and the regeneration loop 14.

In the illustrated embodiment, the system 10 includes an ammonia sensor 64. The ammonia sensor 64 measures the concentration of ammonia (NH3) and/or ammonium (NH4) in the fluid. Ammonia and ammonium are produced by the regeneration sorbent cartridge 32 as a by-product of the urea catalysis urease. The ammonia and ammonium are normally removed by a cation exchanger in the sorbent cartridge 32. However, the dialysis system 10 monitors the fluid for ammonia/ammonium concentrations with the sensor 64 to confirm that the ammonia and ammonium are being removed and remain below safe threshold levels for the patient 16. The total ammonia and ammonium in solution is primarily determined by three parameters: ammonia or ammonium, pH, and solution temperature. By measuring these parameters (or adjusting a parameter, such as adjusting the pH to a desired level), the total amount of ammonia and/or ammonium in the dialysate can be determined.

One sensor 64 according to the present invention is described in a patent application entitled. "Ammonia and Ammonium Sensors," Ser. No. 10/024,170, published as U.S. Pub. No. 2003/0113931, now abandoned, incorporated herein by reference. The sensor 64 determines the total ammonia and ammonium content of an aqueous solution. The sensor 64 includes a hydrophobic ammonia sensing membrane, a pH indicator or conditioner, a temperature sensor and an optical sensor. An algorithm stored in the controller calculates the combined ammonia and ammonium content from the three parameters (e.g., NH3, pH and temperature). The ammonia gas, which is highly soluble in water, is quantified by the hydrophobic sensing membrane that changes color based on the quantity of ammonia gas diffused into it. A multi-wavelength optical sensor continuously measures the membrane color through a transparent window. The sensor 64 achieves a non-intrusive measurement by the using the optical sensor to monitor color changes in the disposable membrane placed inside the fluid path.

In the illustrated embodiment of FIG. 1, the dialysis system 10 also includes one or more fluid flow measurement devices or volume sensors 66 that measure the volume of the medical fluid pumped either intermittently or cumulatively through one or both of the loops 12 and 14. In an embodiment, the fluid flow measurement device 66 measures the amount of fluid supplied to the patient 16 by the patient loop 12. Additionally or alternatively, the regeneration loop 14 and/or the ultrafiltrate drain line employ one or more fluid flow measurement devices 66 to measure the amount of ultrafiltrate removed from the patient 16. Various types of fluid volume measurement or flowrate devices can be used with the dialysis system 10, such as orifice plates, mass flow meters or other flow measuring devices known to those of skill in the art.

FIG. 1 schematically illustrates one embodiment of a flow measurement device or volume sensing device 66, which includes a capacitance sensor that measures the volume of fluid pumped through a chamber, such as a pump chamber (dotted lines designating the device 66 shown encircling the pumps 19, 24 and 30). The capacitive fluid sensor 66 is disclosed in greater detail in the patent application entitled, "Capacitance Fluid Volume Measurement," Ser. No. 10/054, 487, now U.S. Pat. No. 7,107,837, incorporated herein by reference.

The capacitance C between two capacitor plates changes according to the function $C=k\times(S/d)$, wherein k is the dielectric constant, S is the surface area of the individual plates and d is the distance between the plates. The capacitance between the plates changes proportionally according to the function $1/(R\times V)$, wherein R is a known resistance and V is the voltage measured across the capacitor plates.

In one embodiment of the capacitance sensor 66, the sensor cooperates with the pump chamber. The pump chamber in an embodiment includes shells or walls defining a fixed and known volume and a pair of flexible membranes operating between the shells, which expand to fill with fluid and contract to discharge fluid. The capacitance sensor 66 includes capacitor plates disposed on opposite sides of the pump chamber. As the volume of fluid in the chamber or fluid pump changes (i.e., the pump chamber fills or empties), the dielectric property of the varying fluids between the capacitance plates changes. For example, the combined dielectric constant of dialysate and air changes as dialysate replaces air (or air replaces dialysate) within shells of the constant volume chamber. This change in the overall dielectric constant affects a change in the capacitance between the two plates, which causes a change in voltage across the capacitance plates, wherein the change in voltage can be sensed by a voltage sensing device. The controller monitors the change in voltage by the voltage sensing device and correlates (after a calibration of the sensor) the capacitance change to an amount of fluid pumped through the chamber.

In another embodiment, the volume of the chamber or the pump chamber can vary, e.g., by movement of one or both the shells of the chamber. In this embodiment, the capacitance between the capacitor plates changes due to a changing distance d between the plates and/or a changing surface area S of one or more of the plates, wherein the dielectric constant k is static because only one fluid resides at all times between the capacitor plates. In a further alternative embodiment of the measurement device 66, the capacitance C between the capacitor plates changes based on any combination or all three of a change in dielectric constant k, distance d and surface area S.

The controller collects a multitude of voltage signals from capacitance changes from sensor 66 due to a plurality of chamber fill and drain cycles, wherein the controller calculates a total volume of medical fluid pumped over a length of time or number of pump cycles. The capacitance sensor 66 monitors the medical fluid, e.g., dialysate, flow into or from the pump chamber on a real time basis, and in a non-invasive manner.

The capacitance sensor 66 enables the dialysis system 10 to maintain the volume of fluid that is provided to the patient 16 at desirable amounts and flow rates. Maintaining the fluid flow to the patient 16 within desired levels is particularly advantageous for peritoneal dialysis therapies.

Also, it is desirable to maintain the fluid provided to the patient at physiologic levels. Physiologic control, such as sensing and/or adjusting parameters of the fluids, can take place at various locations in the dialysis system 10, including the patient loop 12 and the regeneration loop 14. For example, as mentioned above, the sorbent cartridge 32 may include a pH sensor that adjusts the fluid in the regeneration loop 14, which then adjusts the fluid in the patient loop 12 via the dialyzer to be at a desired physiologic level.

Dual Lumen Connector

Referring now to FIG. 2, one embodiment of a dual lumen patient fluid connector 20 of the present invention is described in further detail. As described above, the dual lumen connector 20 includes a housing 70 having a lumen 72 for providing fluid to the patient lumen and a separate lumen 74 to remove fluid from the patient. Separate housings each having one of the lumens 72 and 74 may be provided. The patient inflow lumen 72 connects to a patient inflow tube 76 of the patient loop 12. Similarly, the patient outflow lumen 74 connects to a patient outflow tube 78 of the patient loop 12. A removable end cap 80 is provided to seal a cavity 82 defined by the housing 70. The cavity 82 surrounds or abuts the lumens 72 and 74 and provides a connection area for the dual lumen catheter 22 (FIG. 1) to insert into the cavity 82 and mate with the lumens 72 and 74.

The housing 70, lumens 72 and 74 and the end cap 80, in an embodiment, are made of any material suitable for medical applications, such as plastic for example. In an embodiment, one of the lumens, e.g., the patient inflow lumen 72 extends further into the cavity 82 than the other lumen, which helps facilitate mating of the connector 20 to the catheter 22. In another embodiment both lumens 72 and 74 extend into the cavity 82 the same or different distance.

The dialysis system 10, particularly the patient loop 12, can be primed, e.g., filled, with the end cap 80 in sealing engagement with the housing 70. The arrows 84 and 86 figuratively illustrate the recirculating fluid flow through the dual lumen connector 20. The system 10 can therefore run without a fluid connection to the patient. Also, the system 10 may include a patient by-pass line between the patient inflow and outflow tubes 76, 78 to allow fluid flow through the patient loop 12 while by-passing the patient 16. The end cap 80 is removed, e.g., pulled off or unscrewed, to expose the cavity 82 and the patient inflow and outflow lumens 72 and 74, respectively, for connection to the dual lumen catheter 22.

In an alternative embodiment, the patient fluid loop 12 directly connects to the dual lumen catheter 22 or to two separate single lumen catheters. In a further alternative embodiment, the connector 20 is adapted to connect to two separate single lumen catheters. In yet another alternative embodiment, two separate connectors link single lumen catheters to incoming and outgoing lines of the patient fluid loop 12. Other configurations are also contemplated by the present invention.

Alternative Dual Loop System with Balanced Flow

Referring now to FIG. 3, a system 100 for providing dialysis treatment to a patient is illustrated. The system 100 of FIG. 3 includes many of the same components as the system 10 of FIG. 1. For example, the system 100 includes two loops, a patient loop 12 and a regeneration loop 14. The patient loop 12 passes a medical fluid, dialysate or blood, to and from a patient 16. In a peritoneal dialysis embodiment, the patient loop 12 and regeneration loop 14 are initially filled and primed with dialysate from a dialysate bag 18. The patient loop 12 fluidly connects to the patient 16 by the multi-lumen patient fluid connector 20 described above in connection with FIG. 2. In a peritoneal dialysis embodiment, the multi-lumen connector 20 connects to a dual lumen catheter 22. In a hemodialysis embodiment, the patient loop 12 fluidly connects to a multi-lumen hemodialysis needle or other patient blood access device.

The system 100 includes multiple patient fluid pumps 24a and 24b. It has been found that using multiple pumps, such as the patient fluid pumps 24a and 24b, creates a steadier flow of fluid to and from the patient 16 within the patient loop 12. For example, fluid may be exiting the fluid pump 24a while the fluid pump 24b is filling with fluid. Balance chambers can be provided, in an embodiment, to balance fluid flow.

The system 100 includes the dialyzer 26 having the dialyzer membrane 28. The spent dialysate (or blood in a hemodialysis embodiment) laden with waste and excess water in the patient fluid loop 12 is cleaned or regenerated when recirculated through the dialyzer 26. The waste passes from the patient loop 12 across the dialyzer membrane 28 to the regeneration loop 14. In the regeneration loop 14, the fluid pumps 30, 30 continuously pump the regenerating dialysate through the combination device 102, which includes the absorbent cartridge 32 and the gas separator 50. The system 100 includes dual dialysate fluid pumps 30 to provide balanced flow within the regeneration loop 14. That is, one of the fluid pumps 30 is being emptied of fluid while the other pump 30 is being filled with fluid. In an embodiment, balance chambers can be provided for balancing fluid flow.

The system 100 can drain ultrafiltrate and other fluids into the drain bag 38. An ultrafiltrate pump 19 pumps the ultrafiltrate and fluids from the patient loop 12 or the regeneration loop 14, for example through valves 40 and 42, into the drain 38. The system 100 also provides the ability to collect fluid in a twenty-four hour collection bag 39 for evaluation of the dialysis therapy.

In an embodiment, one of the patient fluid pumps 24a or 24b pulls dialysate fluid from either the dialysate bag or container 18 or the last bag 21. The last bag 21 includes a volume of fluid that is placed in the patient's peritoneal cavity just prior to the end of the dialysis treatment. The patient with the dialysate from the last bag 21 in the peritoneal cavity disconnects from the system 100 and is able to perform daily activities. The next dialysis therapy begins with draining the last bag from the patient.

The system 100 includes a concentrate container 44, a concentrate pump 46 and valves 48. The concentrate pump 46 provides concentrate from the concentrate container 44 to the regeneration loop 14, for example into the fluid line exiting from the outlet 36 of the combination absorbent cartridge and vent 102. The concentrate container 44 supplies necessary compounds, such as electrolytes and osmotic agents, to the regeneration loop 14 of the system 100 to maintain the desired concentrations of those components.

Besides the concentrate that is contained in the concentrate container 44, the system 100 regenerates dialysate through the regeneration loop 14 and does not require fluids from an outside source. Hence the system 100, as are each of the systems described herein, is completely closed to the outside. The systems of the present invention are thus "closed loop systems". The closed loop nature of the patient loop 12 and the regeneration loop 14 enables the loops to run continuously without absorbing or gathering outside contaminants. The closed loop systems of the present invention also maintain sterility by preventing contamination from the environment.

The system 100, like the system 10, may generate gases over time, such as air and CO2. The system 100 provides a plurality of gas sensors 52 that detect the various gases that may be in the system 100. In the system 100, the gas sensors 52 are provided at an air separator which separates gas from the fluid in the patient loop 12. A gas separation line 51 feeds the separated gas from the patient loop 12 to the inlet side 34 of the combination absorbent cartridge and gas separator device 102. The gas is then purged out of the system 100 by the gas separator 50. The gas separator 50 maintains the closed loop structure of the system 100 by preventing contaminants from entering the system 100. For example, the gas separator 50 can include a microbial filter which allows gas to exit the system 100, but prevents contaminants from entering the system 100. In another embodiment, the gas from the patient loop 12 may be purged from the system 100 by a separate gas purge device at the patient loop 12. The gas sensors 52, in an embodiment, can send an electronic signal to the controller (not illustrated). When the controller detects gas, the controller causes one or more valves to open, wherein the gas from the loop 12 is fed to a one-way vent and purged from the system 100.

The system 100 further includes the inline heater 54, which, in an embodiment, includes an infrared or radiant heater 56 and a plate heater 58 as described above. In an embodiment, the heater 54 has an air separator which allows air to exit port 59 on be purged from the system.

The system 100 further includes an orifice device 61 that stabilizes the differential pressure in the dialyzer 26 across the membrane 28. That is, the orifice device 61 can restrict the flow in the patient loop 12 to create a pressure differential between the patient side and regeneration side of the dialyzer 26. The pressure gradient or differential occurs across the membrane 28 in which the patient loop 12 having a higher fluid pressure than the regeneration loop 14. The orifice device can be a fixed or variable flow restriction and can provide a fixed or variable pressure differential. Also, the orifice device 61 can be electrically coupled to and operated by the controller, which can activate, e.g., open or close the orifice device as necessary.

The pressure differential across the membrane 28 (higher pressure in the patient loop 12 and lower pressure in the regeneration loop 14) created by the orifice 61 assists in maintaining a greater pressure in the regeneration loop 14 relative to atmosphere pressure external to the system 100. The positive pressure in the regeneration loop 14 relative to the external atmosphere pressure aids in ensuring that external air is not pulled from the surrounding environment through the air vent 50 into the regeneration loop 14, i.e., air can only exit the system 100 and not enter into the system 100. Accordingly, the orifice 61 contributes to the closed loop nature of the system 100.

The system 100 provides a number of temperature sensors, such as sensors 63, 65 and 67, which monitor temperatures at various points within the patient loop 12. The controller uses the sensed temperatures to maintain a desired temperature within the patient loop 12. As illustrated, the temperature sensor 63 is located at or on the heater 54, which enables the system 100 to sense a temperature at a point very close to the constituent heaters 56 and 58, and to control the heaters 56, 58.

The system 100 further includes one or more pressure sensors 60 and 62, which reside at various points along the patient fluid loop 12. The pressure sensors 60 and 62 can be used to prevent excessive positive or negative pressures from being applied to the patient. The pressure within the system can be controlled by, e.g., activation of the patient fluid pumps 24a, 24b.

The system 100 also monitors the absorbent cartridge 32 with an ammonia/ammonium sensor. Sample fluid exiting the absorbent cartridge 32 can be directed through a pH adjuster 71 to force the ammonia/ammonium equilibrium balance to a particular level. The amount of ammonia and/or ammonium in the sample fluid is measured by a sensor 73. Accordingly, the effectiveness of the cartridge 32 to remove ammonia/ammonium after conversion from urea can be monitored. When the concentration of ammonia and/or ammonium reaches a threshold level, the system can produce a signal, or take other action such as shutting down, that indicates the cartridge 32 needs to be replaced.

Of course, the system 100 can monitor other fluid parameters and take appropriate action, as desired. Also, sample fluid can be taken at any desired location in the system 100. Further, fluids in the patient and regeneration loops 12, 14 can be tested or monitored directly rather than taking samples.

The system 100 also includes fluid volume sensors 66 which in an embodiment are capacitance sensors that sense a change in capacitance occurring between two capacitor plates. The capacitor plates surround the pumps 24 of the patient loop 12, the pumps 30 of the regeneration loop 14 and the pumps leading to the fluid containers. Each of the pumps 24a, 24b, pump 30, pump 19 and pump 46 can be provided with the capacitance volume sensor 66 of the present invention. Each of the sensors 66 sends a discrete signal to the controller (not illustrated), which measures and monitors the volume of fluid flowing through the pump chambers of the respective pumps. In other embodiments, any suitable fluid volume measurement device can be used.

Alternative Dual Loop System with Gas Separation

Figure 4:
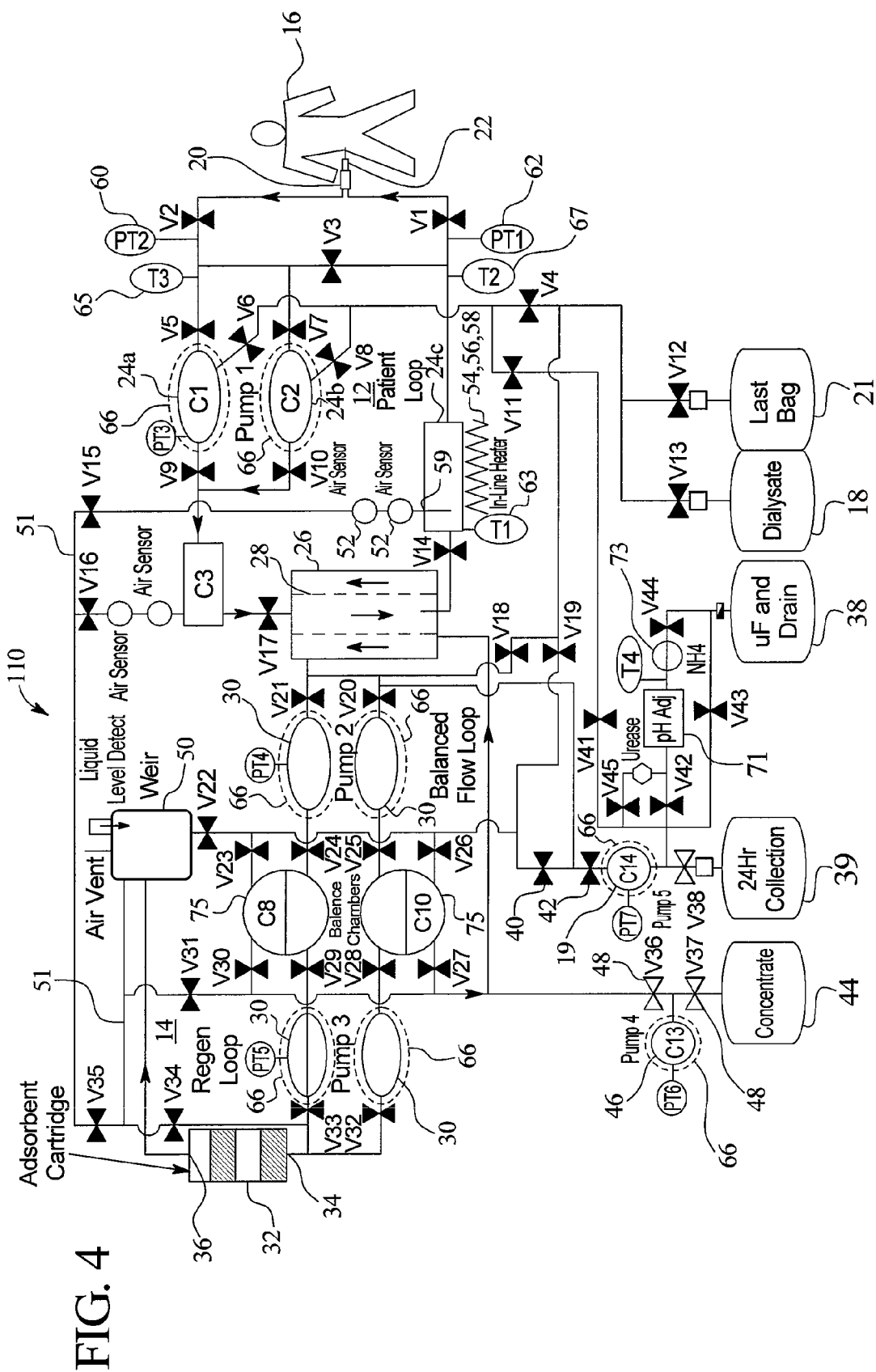
FIG. 4 schematically illustrates a further embodiment of a dialysis system according to the principles of the present invention.

Referring now to FIG. 4, a system 110 of the present invention is illustrated. The system 110 of FIG. 4 is similar to the system 100 of the FIG. 3 and is a closed loop system. The system 110 includes various components of the system 100 described previously. The system 110 has a regeneration loop 14 which has a pair of balanced dialysate fluid pumps created by a pair of chambers 75 that operate with the pumps 30. Each balance chamber 75 includes a pair of chambers separated by a membrane. When one of the pumps 30 fills one side of the chambers of the balance chambers 75 fills with medical fluid, the membrane is forced toward the other chamber, which forces fluid out of that chamber. In this way, the membrane acts to balance the flow of the dialysate fluid within the regeneration loop 14, so that there is no net flow of fluid across the dialyzer membrane except for the flow needed to replace the fluid removed by the ultrafiltrate pump 19.

Another difference of the system 110 of FIG. 4 compared to the system 100 of FIG. 3 is the gas separator 50. The gas separator 50 in the illustrated embodiment of the system 110 is independent of the sorbent cartridge 32. The gas separator 50 accepts gas through a vent line 51 that runs from the exit port 59 of the heater 54 in the patient fluid loop 12. One or more gas sensors 52 monitor gas in the vent line 51 as illustrated.

Disposable Cassettes

Figure 5:
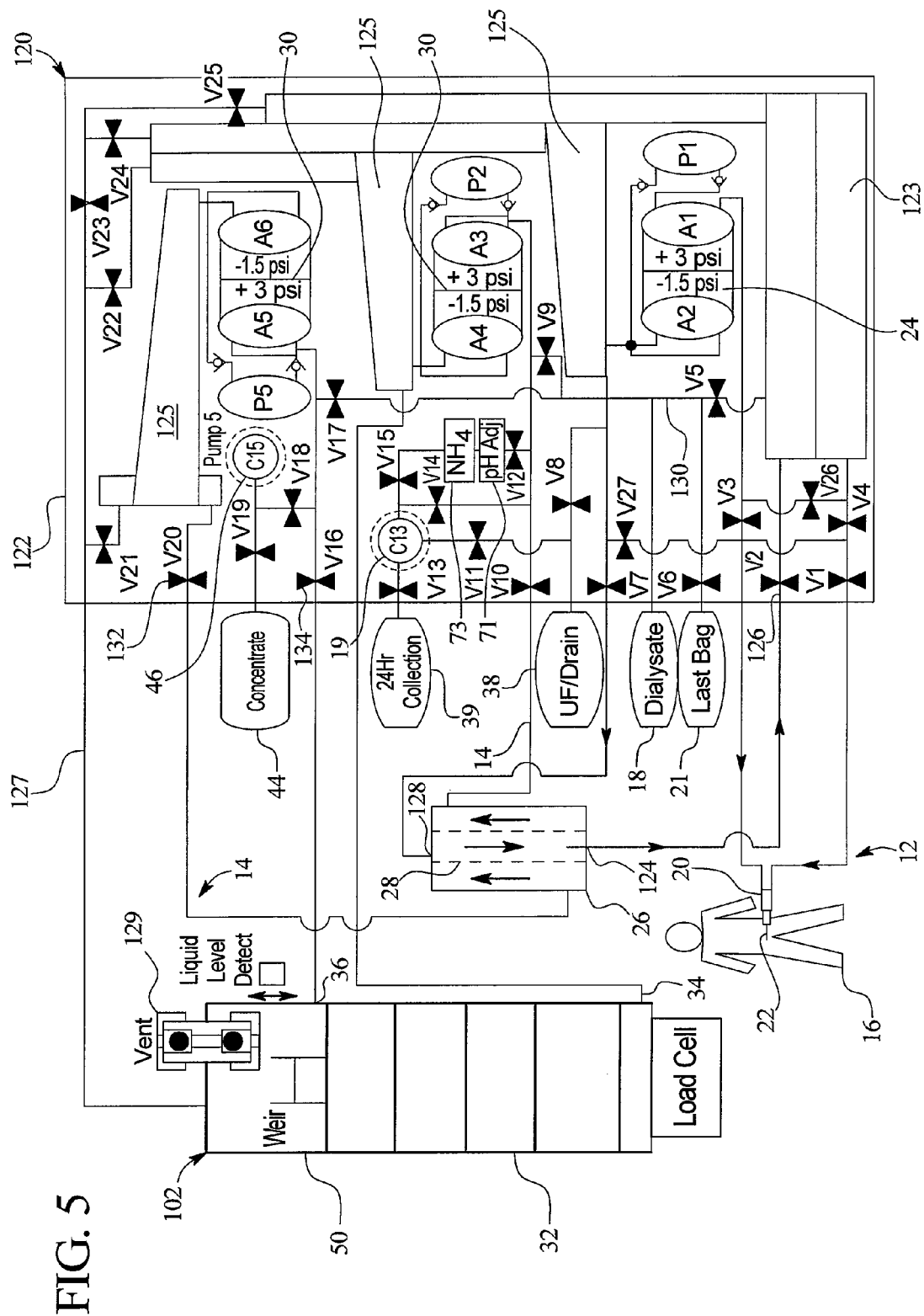
FIG. 5 illustrates an embodiment of a disposable cassette according to the present invention.

Referring now to FIG. 5, a dialysis system having a disposable cassette 120 according to the present invention is illustrated. In this variation of the system 100 of FIG. 3, the pumps 30 of system 120 draw fluid from accumulators A4 and A6 and discharge into accumulators A3 and A5. Accumulators A3 to A6 smoothen the dialysate flow by dampening pressure fluctuations during pumping. In an embodiment, much of the flow logic and at least parts of the flow devices described above are provided in the disposable cassette 120. The cassette 120, in an embodiment, has a rigid plastic body 122 with various fluid flow channels and fluid chambers defined in the body 122. A flexible membrane is bonded to the front side of the cassette body 122 shown in FIG. 5. The membrane covers the fluid channels and chambers and is sealed to the body 122 around the channels and chambers. Accordingly, the membrane forms a wall of the fluid flow paths and fluid chambers. Similarly, the back side of the cassette body 122 may also be covered with a membrane.

The body 122, in an embodiment, is approximately 12 inches high, eight inches wide, and one inch deep. The flow components and flow lines defined by the body 122 fluidly connect to other system components. Also, pump actuators, valve actuators, sensors and other system components may interface with the cassette 120.

Specifically, the body 122 provides a portion of the closed patient the regeneration loops 12 and 14. The dual lumen catheter 22 that inserts into the peritoneal cavity of the patient 16 connects to the dual lumen connector 20 outside of the body 122 of the disposable cassette 120. The patient loop 12 extends from an exit port 124 of the dialyzer 26 to a valve chamber 126 defined by the body 122. The patient fluid loop 12 includes a series of manifolds and fluid flow paths that fluidly connect to the patient fluid pump(s) 24. The patient fluid pump 24 pumps the dialysate through the patient 16 and into an inlet 128 of the dialyzer 26.

The patient fluid loop 12 also connects via pathways defined by the body 122 of the disposable cassette 120 to various medical fluid bags. For instance, the dialysate fluid bag 18, which is maintained outside of the disposable cassette 120, fluidly connects to a line 130 leading to the patient fluid loop 12. Similarly, the last bag 21 also connects via a line defined by the body 122 to the line 130 that fluidly communicates with the patient fluid loop 12. The line 130 defined by the body 122 also fluidly communicates with the ultrafiltrate drain 38.

The body 122 of the disposable cassette 120 also defines chambers for the concentrate pump 46 and the ultrafiltrate pump 19. The concentrate pump 46 fluidly connects to an external concentrate bag 44. The twenty-four hour collection bag 39 described above fluidly connects along with the drain 38 to a fluid line defined by the body 122 that runs to the ultrafiltrate pump 19.

The disposable cassette 120 provides fluid flow paths and defines chambers and other types of fluid orifices for the fluid flow components described above. Specifically, the body 122 of the disposable cassette 120 defines a patient fluid pump chamber 24 and dialysate fluid pump chambers 30. The disposable cassette 120 mounts to a separate non-disposable housing that includes the mechanical workings of the flow components, such as the pumps. The pump chambers are bounded on one side by a flexible membrane (not illustrated) that is positioned adjacent to and driven by the pump plungers of the non-disposable housing.

At least one side of the cassette 120 is covered with the flexible, e.g., plastic membrane (not illustrated). The disposable cassette 120 plugs into a cavity or portion of the non-disposable housing (not illustrated). The housing provides the actuators for each of the pumps herein described, e.g., the patient pumps 24, the dialysate pumps 30, the ultrafiltrate pump 19 and the concentrate pump 46. The housing also provides the actuators for the various valve chambers defined by the body 122 of the cassette 120, e.g., valve chamber 126. The more expensive mechanical and electromechanical pieces of the flow components, e.g., the pump actuators and valve actuators, are kept and reused in the housing.

The disposable cassette 120 provides sterile, disposable fluid pathways, such as the pump chambers and the valve chambers. The actuators of the non-disposable housing press against the flexible plastic membrane at the pump chambers and valve chambers to force or allow fluid through the system. When the pump actuator pulls back from pressing against the membrane, the membrane returns to its normal shape and no longer exerts a force on the fluid within the pump chamber. The pump chamber fills with fluid as the membrane is drawn back. Also, the membrane can be positively drawn back by, for example, the pump actuator or vacuum pressure. The pump has thus made a cycle.

The body 122 of the disposable cassette 120 also defines at least a portion of a mounting area for housing the ammonia, ammonium or pH sensors or adjustors. In the illustrated embodiment, the disposable cassette 120 defines an area for housing the pH adjustor 71 and a disposable colormetric membrane (which changes color based on the ammonia/ammonium concentration) of the ammonia/ammonium sensor 73, wherein the fluid within the body 122 of the cassette 120 can fluidly communicate with the sensor. The optical color reader of the ammonia/ammonium sensor 64 is disposed in the non-disposable housing (not illustrated), wherein the sensor can receive electrical power as needed. If a pH sensor is used instead of the pH adjustor 71, a reusable portion of the pH sensor can also be located in the housing.

The housing also provides the in-line heater 54 and in an embodiment provides one of either the radiant heater 56 and the plate heater 58, which is described in detail in the patent application entitled, "Medical Fluid Heater Using Radiant Energy," Ser. No. 10/051,609, now U.S. Pat. No. 7,153,285, mentioned above. Further, the housing provides one of the capacitor plates of the fluid volume sensor 66 beneath one or more of the pump actuators, as described in detail in the patent application entitled, "Capacitance Fluid Volume Measurement," Ser. No. 10/054,487, now U.S. Pat. No. 7,107,837, mentioned above.

Referring back to the cassette 120 of FIG. 5, the cassette 120 has an in-line heating fluid heating path 123 for heating the fluid. The fluid in the heating path 123 is heated by a heater external to the cassette.

The cassette 120 also has one or more gas separators 125 which separate gas from fluid in the cassette 120. The gas separators 125 feed the separated gas through a line 127 to a vent 129.

The closed loop system of the present invention enables at least one waste component to pass through the membrane 28 of the dialyzer 26 from the patient fluid loop 12 to the regeneration loop 14. The patient loop 12 extending outside of the body 122 fluidly connects to a valve chamber 132 defined by the body 122. The regeneration loop 14 includes manifold sections defined by the body 122 and leads to pump chambers 30. The closed loop system prevents air or other fluids from entering the system.

The pump chambers 30 fluidly communicate with the sorbent chemical cartridge 32 and the gas separator 50 of the combined device 102. The regeneration loop 14 extends from the outlet 36 of the combined device 102 and returns to the body 122 of the disposable cassette 120 through the valve chamber 134. From the valve chamber 134, the regenerated dialysate is pumped through the pump chambers 30 and into the manifold system defined by the body 122.

Figure 6:
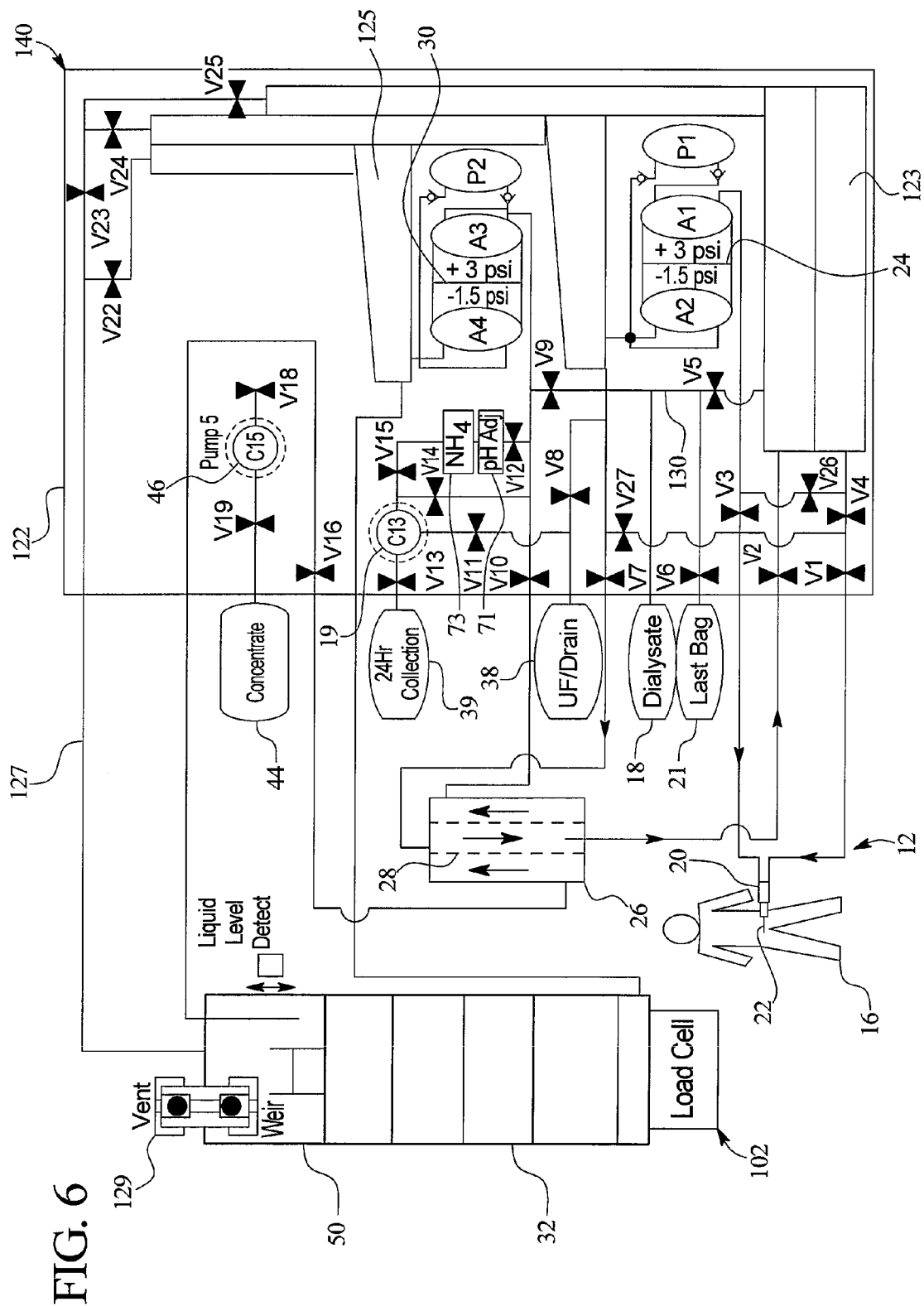
FIG. 6 illustrates another embodiment of a disposable cassette according to the present invention.

Referring now to FIG. 6, another closed loop system having another disposable cassette 140 is illustrated. This embodiment of the disposable cassette 140 of the present invention includes many of the same flow components and flow chambers as the cassette 120 of FIG. 5. The cassette 140, however, only includes a single regeneration pump body 30. The cassette 140 in general, is less complicated than the cassette 120 and illustrates that the disposable cassettes of the present invention may be adapted for different embodiments of the closed loop dialysate regeneration systems described herein.

Like the cassette 120 of FIG. 5, at least one side of the cassette 140 is covered with a flexible, e.g., plastic membrane (not illustrated). The disposable cassette 140 plugs into a non-disposable housing (not illustrated) that provides the actuators for the various pumps, e.g., the patient pump 24, the dialysate pump 30, the ultrafiltrate pump 19 and the concentrate pump 46. The housing also provides the actuators for the various valve chambers defined by the body 122 of the cassette 140. The more expensive mechanical and electromechanical pieces of the flow components, e.g., the pump actuators, are again kept and reused in the housing. As described above, the actuators press against the flexible plastic membrane at the pump chambers to force fluid through the system.

As illustrated in both FIGS. 5 and 6, the disposable cassette 120 or 140, in combination with certain external devices such as the dialyzer 26, sorbent cartridge and gas separator device 102 and the fill and drain bags, provides completely closed loop systems. The only make-up or additional fluid that the regeneration system uses is that of the concentrate from the concentrate bag 44, which seals to a device within the body 122 of the cassettes 120 and 140. Also, other than the systems being connected to a patient, fluids and air cannot enter the closed loop system.

Figure 7:
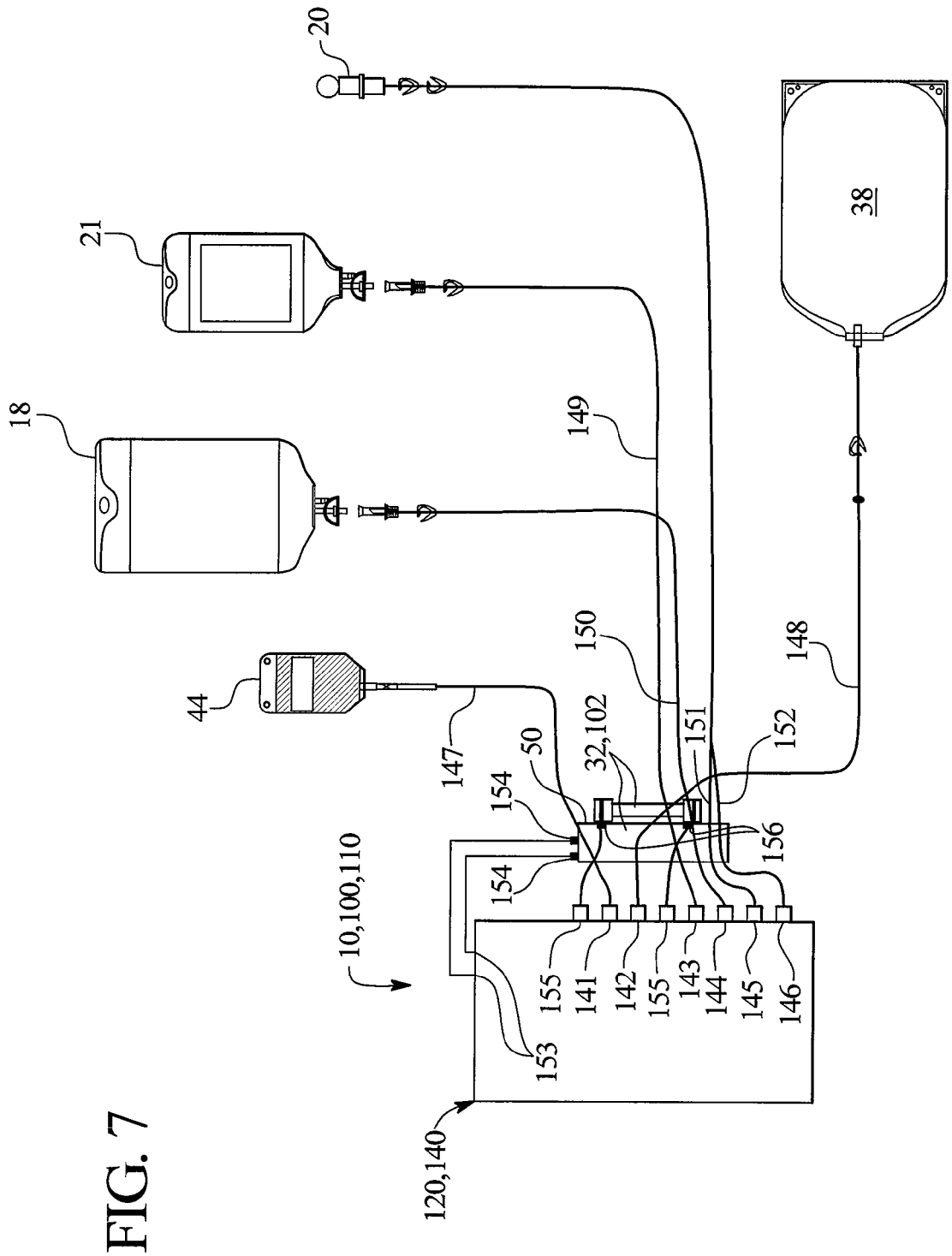
FIG. 7 illustrates a disposable cassette of the present invention connected to various fluid containers.

Referring now to FIG. 7, a schematic diagram illustrates the different physical components of a disposable set of the regeneration systems of the present invention. The disposable set is intended to be used for a single dialysis therapy and then discarded. Another disposable set is used for the next dialysis therapy. Each of the above-described systems 10, 100 and 110 in an embodiment includes a disposable cassette, such as the cassette 120 or 140. The disposable cassette 120 or 140 provides a port 141 that connects to the concentrate bag 44 via a line 147. The cassette provides a port 142 that fluidly connects to the drain bag 38 via a line 148. The cassette provides a port 143 that fluidly connects to the last bag 21 via a line 149. The cassette defines a port 144 that fluidly connects to the dialysate bag 18 via a line 150. The cassette provides ports 145 and 146 that run to and from the dual lumen connector 20 via patient lines 151 and 152, respectively.

In an embodiment, each of the lines 147 to 152 are made of medical grade tubing, such as a flexible, sterile and inert plastic such as polyethylene, polystyrene, polypropylene or polyvinylchloride ("PVC"). In an embodiment, the bags and the lines are clear so that the patient or operator can see fluids traveling from the bags and through the lines to a cassette 120 or 140. The lines 147 to 152 connect to the ports 141 to 146 via any type of medical fluid connection known to those of skill in the art. In an embodiment, the connections are quick-type connections that enable the patient or operator to easily remove the line from its mating port.

The disposable cassette 120 or 140 includes at least one port 153 that fluidly connects to at least one outlet port 154 of the gas separator 50 or combination device 102. The disposable cassette 120 or 140 includes at least one port 155 that fluidly connects to at least one inlet port 156 of the sorbent cartridge 32 or combination device 102. The lines connecting the disposable cassette 120 or 140 to the sorbent cartridge 32, gas separator 50 or combination device 102 including same are made of medical grade tubing, such as a flexible, sterile and inert plastic such as polyethylene, polystyrene, polypropylene or polyvinyl chloride.

Alternative Dual Loop System

Figure 8:
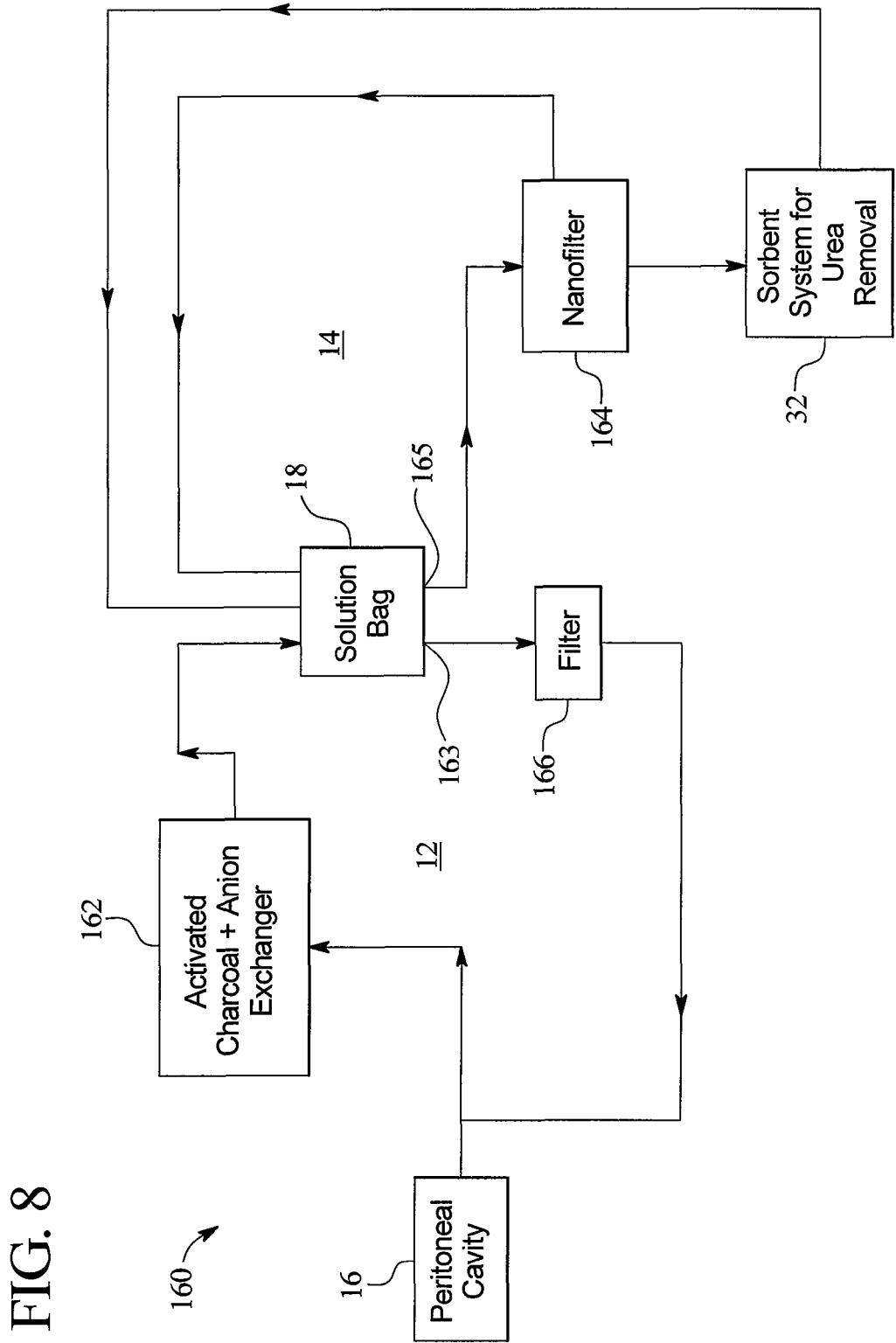
FIG. 8 schematically illustrates yet another embodiment of a dialysis system according to the principles of the present invention.

Referring now to FIG. 8, an alternative closed loop regenerative system 160 is illustrated. The system 160 is shown schematically, however, the system 160 may employ the disposable set described above such as the disposable cassette, the fluid pumps, the various sensors, valves and controller. The system 160 includes a patient fluid loop 12 and a regeneration loop 14.

When dialysate is removed from the peritoneal cavity of the patient 16, the solution passes through an activated charcoal and anion exchanger 162. The activated charcoal of the filter or exchanger 162 removes uric acid, creatinine, small molecular weight organics and middle molecules. The anion exchange column of the exchanger 162 removes phosphate. The solution exiting the filter or exchanger 162 enters a solution or dialysate bag 18. The dialysate entering the solution bag 18 has two possible places to exit. One possibility includes exiting the solution bag 18 from a port 163, entering a filter 166 and returning to the peritoneal cavity of the patient 16. Mother possibility includes exiting the solution bag 18 at a port 165 and entering a nanofilter 164. The system 160 splits the dialysate fluid exiting the solution bag or container 18.

The nanofilter 164 operates similar to the dialyzer 26 described above. The nanofilter 164 includes a membrane. The membrane of the nanofilter 164 rejects most electrolytes, i.e., allows most of the electrolytes to return to the solution bag. The nanofilter 164, however, filters most all of the urea and a small amount of sodium through the membrane and into a sorbent system cartridge 32, which is similar to the sorbent cartridges described above. The sorbent cartridge 32 as described above absorbs and the urea from the fluid that is able to permeate through the membrane of the nanofilter 164.

A plurality of pumps (not illustrated) are provided to individually circulate medical fluid or dialysate through the patient loop 12 and the regeneration loop 14. The pump or pumps that control the recirculation through the regeneration loop 14 are adapted to circulate the regenerating fluid at a different flow rate, i.e. much faster, than the flow rate of fluid pumped through the patient loop 12. It is believed that by using this method, the need for a concentration bag such as the concentration bags 44 described above would not be needed. Thus, it should be appreciated that the system 160 is a closed loop system that does not require any sort of make-up materials or any continuous source of outside fluid. The system 160 is therefore very adept at keeping air and other contaminants from entering the system.

In an alternative embodiment, the a reverse osmosis membrane or an electrooxidation system replaces the sorbent cartridge 32. In this alternative embodiment, a reconstitution or concentration bag, such as the concentration bag 44, is likely to be necessary.

The regeneration loop 14 removes urea at a rate of approximately 50 to 80%. The dialysate returns to the peritoneal cavity of the patient 16 substantially free from uric acid, creatinine, small molecular weight organics and middle molecules. Further, the nanofilter 164 can reject calcium magnesium at a rate of approximately 98% and glucose at a rate of approximately 80%. The permeate stream exiting the nanofilter 164 includes urea, approximately 70% sodium chloride and approximately 20% glucose. It should be appreciated that the system 160 is useful for performing continuous flow peritoneal dialysis.

Dual Loop System for Hemodialysis

Figure 9:
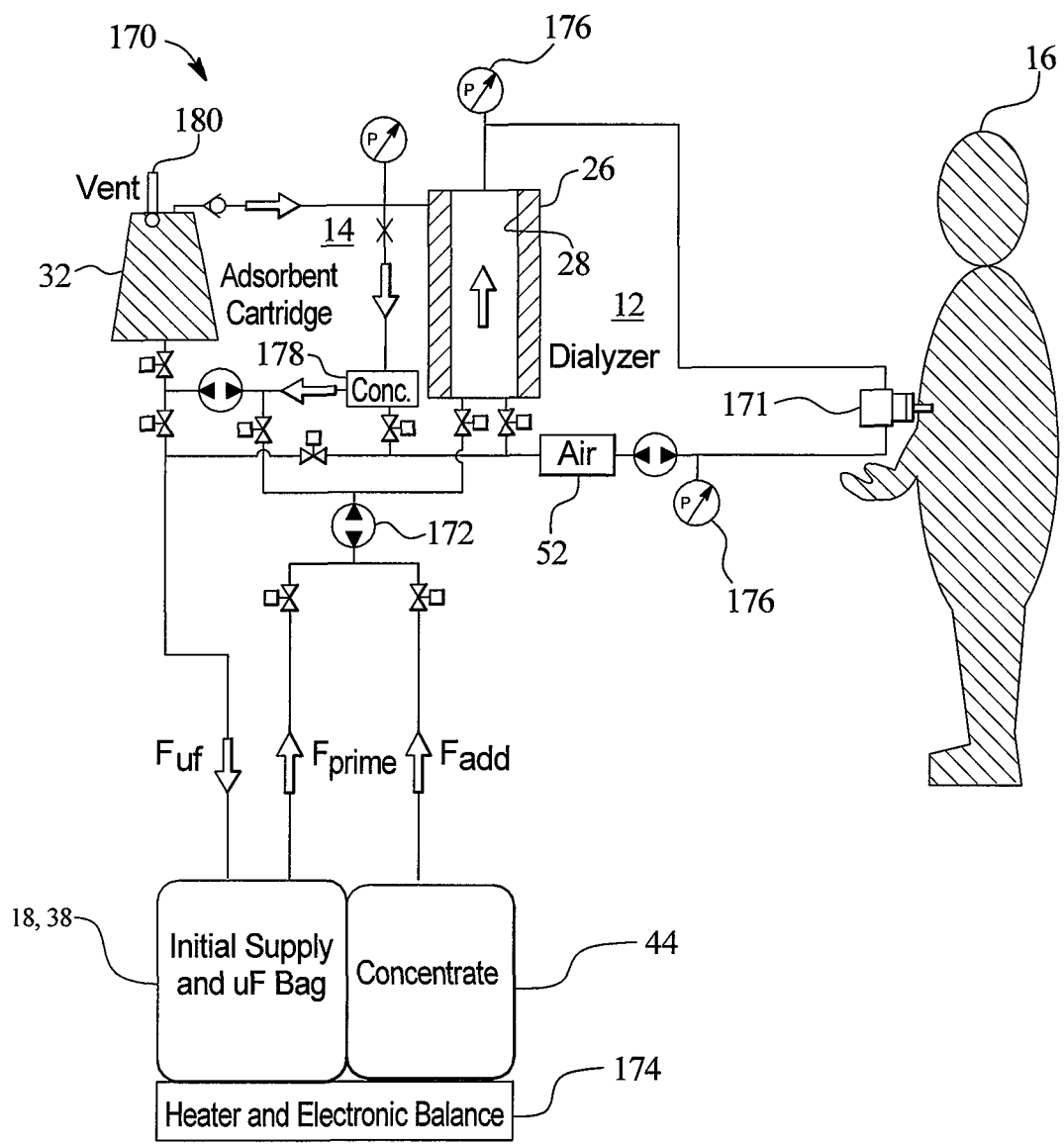
FIG. 9 schematically illustrates an embodiment of a dialysis system according to the principles of the present invention that provides hemodialysis.

Referring now to FIG. 9, a system 170 is illustrated. Each of the previous systems 10, 100 and 110 of FIGS. 1, 3 and 4, respectively, can be used for peritoneal dialysis or hemodialysis. However, each of the systems described above has been primarily described and illustrated using peritoneal dialysis, that is, the patient loop has been illustrated using a dialysis solution. The system 170 illustrates that the dual lumen catheter or two single lumen catheters can be replaced by a hemodialysis needle 171, which connects to the arm (or other suitable portion) of the patient 16 to withdraw blood through the hemodialysis needle 171.

The system 170 illustrates that the patient's blood flows through the patient loop 12 while dialysate flows through the regeneration loop 14. The patient's blood flows along one side of the membrane 28 of the dialyzer 26, while the dialysate flows along the outside or other side of the membrane 28 of the dialyzer 26. The waste components and ultrafiltrate transfer from the patient's blood in the patient loop 12, through the membrane 28, into the dialysate in the regeneration loop 14.

The system 170 includes a fixed volume recirculating regeneration loop 14 that dialyzes the patient fluid loop 12. A single pump 172 operates to remove the ultrafiltrate from the patient 16 to the ultrafiltrate container 38. The pump 172 adds dialysis fluid from the dialysis bag 18 or concentrate from the concentrate bag 44 to the regeneration loop 14. In an alternative embodiment, the concentrate can be metered into the dialysate of the regeneration loop 14 as a solid prior to or during therapy.

As an alternative to the capacitance volume sensing described above, the volume of dialysate fluid flowing through the regeneration loop 14 can be determined using an electronic balance 174 illustrated below the dialysate bags. The electronic balance 174 keeps track of the amount of dialysate that is supplied to the system during a priming of the system. The electronic balance 174 also monitors any additional dialysate added to the patient loop 12 during dialysis treatment. The electronic balance 174 measures the amount of ultrafiltrate that is withdrawn from the system and the amount of the concentrate that is added from the concentrate bag 44. In other alternative embodiments, any of the systems described herein can be sensed using other types of flowmeters or devices employing Boyle's Law known to those of skill in the art.

The system 170 removes ultrafiltrate by opening a valve chamber and transferring a known volume of the fluid into the ultrafiltrate bag 38. The removal of fluid creates a pressure differential across the membrane 28 of the dialyzer 26, which causes fluid to filter through the dialyzer membrane 28 and into the regeneration circuit 14. Sterile dialysate from a supply bag 18 is infused into the patient circuit 12 as required. Concentrate from the concentrate bag 44 can also be infused into the regenerating circuit 14 as needed. Pressure sensors 176 monitor and control the rate at which the system 170 draws ultrafiltrate into the container 38.

Gas sensors 52 are used to prevent air from being delivered to the patient 16. In an embodiment, a multi-analyte sensor 178 is employed to monitor the concentration of electrolytes in the regenerated dialysate as well as the efficiency of the regeneration system in removing uremic toxins. The output of the multi-analyte sensor 178 controls the rate of reconstitution from the concentrate bag 44, the efficiency of the regeneration system and can detect the presence of a leak in the dialyzer. A vent 180 vents air that becomes trapped in the system or $CO_2$ that is generated by the absorbent cartridge 32. In an alternative embodiment, an automated valve that is provided integrally with the adsorbent cartridge 32 replaces the mechanical vent 180.

Although the system 170 is illustrated as a hemodialysis system, the system 170 is easily converted to a peritoneal dialysis system by placing the catheter into the patient's peritoneal cavity and by running dialysate through the patient loop 12 as opposed to the patient's blood. The ultrafiltrate bag 38, the dialysate container 18 and the concentrate container 44 each fluidly connect to the regeneration loop 14 and the patient circuit is kept relatively simple. The system 170 is especially conducive for continuous flow of peritoneal dialysis, however, standard APD and TIDAL therapies could be performed in the system 170.

Multi-Purpose Container

Figure 10:
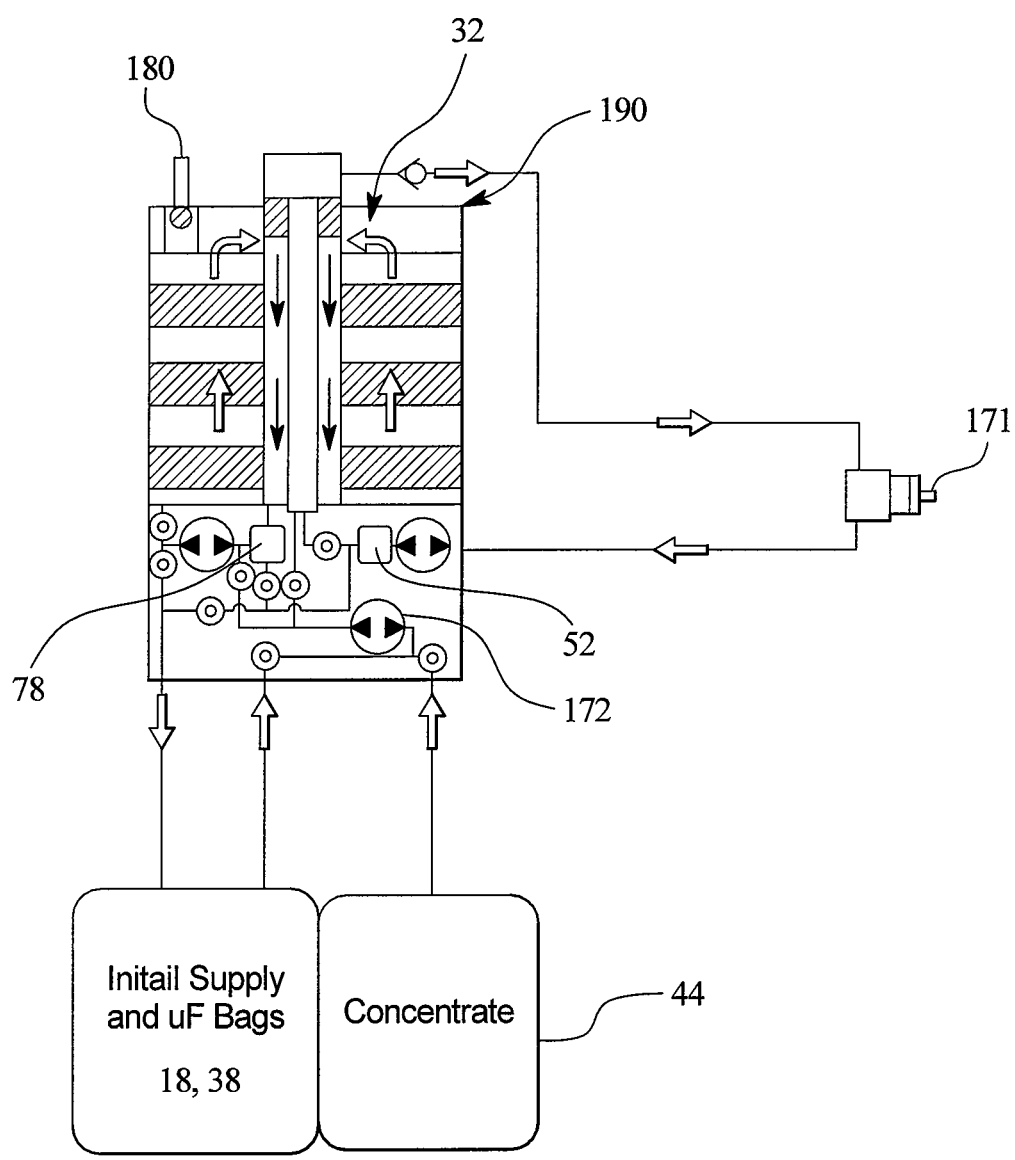
FIG. 10 illustrates a combination container providing various components used in the dialysis systems of the present invention.

Referring now to FIG. 10, a combined absorbent cartridge, pump and valve system is placed into a single container, e.g., a canister, cartridge or cassette 190. The combination container 190 is illustrated as housing the components specifically described in the system 170 of FIG. 9. However, the combination container 190 is adaptable to house the components of any of the above-described systems, namely, the systems 10, 100 and 110. The canister, cartridge or cassette is adaptable to be made of any material such as plastic or metal. The container 190 includes the adsorbent cartridge 32, which is configured as described above. Alternatively, the container includes the combination device 102 that provides the adsorbent cartridge 32 and the gas separator 50.

The container 190 includes the pumps illustrated in FIG. 9 including the pump 172 that enables dialysate to be drawn from the dialysate bag 18 or concentrate to be drawn from the concentrate bag 44. Additionally, the pump 172 enables ultrafiltrate to be drained into the bag 38. In an embodiment, the container 190 includes the multi-analyte sensor 178 and the gas sensor 52, as described in the system 170 of FIG. 9. The container 190 also includes the mechanical or automated vent 180 described in the system 170. Thus, the only devices external to the container 190 are the dialysate bags and the hemodialysis needle 171 that is inserted in the patient's arm or other extremity to perform hemodialysis. Obviously, by the multi-lumen connector 20 and catheter 22 can replace the needle 171 to perform peritoneal dialysis.

When the container 190 is provided in the form of a disposable cassette, the cassette 190, like the cassettes 120 and 140 of FIGS. 5 and 6, is covered on at least one side with a flexible, e.g., plastic membrane (not illustrated). The disposable cassette 190 plugs into a non-disposable housing that provides the actuators for the various pumps, e.g. the patient pumps 24, the dialysate pumps 30, the ultrafiltrate pump 19 and the concentrate pump 46. The more expensive mechanical and electromechanical pieces of the flow components, e.g., the pump actuators, are again kept and reused in the housing. The sorbent cartridge 32 and the gas vent 180 can be disposable.

The above specification has been broken down into headings for purposes of readability, clarification and to promote the enablement of the present invention. The headings are in no way intended to limit the combined teachings of the present invention. The features taught under any given heading are not limited to the embodiments disclosed under the heading. The present invention includes any combination of features from the disclosures under the different headings provided herein. Further, while the presently preferred embodiments have been illustrated and described, numerous changes and modifications can be made without significantly departing from the spirit and scope of this invention. Therefore, the inventors intend that such changes and modifications are covered by the appended claims.

The invention is claimed as follows:
1. A hemodialysis system comprising:
  a dialyzer;
  a blood circuit including a blood pump in fluid communication with the dialyzer;

a dialysate circuit including a dialysate circulation pump in fluid communication with the dialyzer, the dialysate circuit further including a sorbent cartridge for cleaning used dialysate;
a container holding an initial supply of dialysate;
a container pump in fluid communication with the dialysate circuit and the container;
a supply of concentrate, wherein the container pump is also positioned and arranged to pump concentrate from the concentrate supply to the dialysate circuit; and
an electronic weight balance positioned and arranged to weigh the supply of concentrate.

2. The hemodialysis system of claim 1, wherein the container doubles as an ultrafiltration collection container.

3. The hemodialysis system of claim 1, wherein the electronic weight balance is positioned and arranged to weigh both the concentrate supply and the container.

4. The hemodialysis system of claim 1, wherein the dialysate circuit includes at least one sensor for sensing a toxin level of dialysate flowing through the dialysate circuit.

5. The hemodialysis system of claim 4, wherein an output from the sensor is used to control a rate of reconstitution from the supply of concentrate.

6. The hemodialysis system of claim 1, wherein the dialysate circuit is vented.

7. The hemodialysis system of claim 6, wherein the dialysate circuit is vented at the sorbent cartridge.

8. A hemodialysis system comprising:
a dialyzer;
a blood circuit including a blood pump in fluid communication with the dialyzer;
a dialysate circuit including a dialysate circulation pump in fluid communication with the dialyzer, the dialysate circuit further including a sorbent cartridge for cleaning used dialysate;
a container holding an initial supply of dialysate;
a supply of concentrate;
a concentrate pump positioned and arranged to pump concentrate from the concentrate supply to the dialysate circuit; and
an electronic weight balance positioned and arranged to weigh the dialysate supply container.

9. The hemodialysis system of claim 8, wherein the electronic weight balance is positioned and arranged to weigh both the concentrate supply and the dialysate container.

10. The hemodialysis system of claim 8, wherein the dialysate container doubles as an ultrafiltration collection container.

11. The hemodialysis system of claim 8, which includes a valve configured to selectively allow dialysate removed from the dialyzer to be directed to the sorbent cartridge or to the dialysate container as ultrafiltration.

12. The hemodialysis system of claim 8, which includes a first valve positioned between the dialyzer and the dialysate circulation pump and a second valve positioned between the dialysate circulation pump and the sorbent cartridge.

13. The hemodialysis system of claim 8, which includes a check valve positioned and arranged to prevent regenerated dialysate exiting the sorbent cartridge from reentering the sorbent cartridge.

14. The hemodialysis system of claim 8, which includes a sensor positioned and arranged in the blood circuit for sensing air in the blood circuit.

15. The hemodialysis system of claim 8, which includes a sensor positioned and arranged to monitor regenerated dialysate exiting the sorbent cartridge.

16. The hemodialysis system of claim 8, which includes a sensor positioned and arranged to monitor a toxin removal efficiency of the system.

17. The hemodialysis system of claim 8, which includes a sensor positioned and arranged so that an output of the sensor can be used to control a rate of flow from the supply of concentrate.

18. A hemodialysis system comprising:
a dialyzer;
a blood circuit including a blood pump in fluid communication with the dialyzer;
a dialysate circuit including a dialysate circulation pump in fluid communication with the dialyzer, the dialysate circuit further including a sorbent cartridge for cleaning used dialysate;
a container holding an initial supply of dialysate;
a supply of concentrate;
a concentrate pump positioned and arranged to pump concentrate from the concentrate supply to the dialysate circuit; and
wherein the hemodialysis system is configured to electronically weigh the dialysate supply container.

19. The hemodialysis system of claim 18, which is configured to weigh both the dialysate supply container and the supply of concentrate.

20. A hemodialysis system comprising:
a dialyzer;
a blood circuit including a blood pump in fluid communication with the dialyzer;
a dialysate circuit including a dialysate circulation pump in fluid communication with the dialyzer, the dialysate circuit further including a sorbent cartridge for cleaning used dialysate and at least one sensor for sensing a toxin level of dialysate flowing through the dialysate circuit;
a container holding an initial supply of dialysate;
a container pump in fluid communication with the dialysate circuit and the container;
a supply of concentrate; and
an electronic weight balance positioned and arranged to weigh the supply of concentrate.

21. The hemodialysis system of claim 20, wherein an output from the sensor is used to control a rate of reconstitution from the supply of concentrate.

22. A hemodialysis system comprising:
a dialyzer;
a blood circuit including a blood pump in fluid communication with the dialyzer;
a dialysate circuit including a dialysate circulation pump in fluid communication with the dialyzer, the dialysate circuit further including a sorbent cartridge for cleaning used dialysate, and wherein the dialysate circuit is vented at the sorbent cartridge;
a container holding an initial supply of dialysate;
a container pump in fluid communication with the dialysate circuit and the container;
a supply of concentrate; and
an electronic weight balance positioned and arranged to weigh the supply of concentrate.

\* \* \* \* \*